United States Patent
Fernandes Da Cunha-Vaz et al.

(10) Patent No.: US 11,234,591 B2
(45) Date of Patent: Feb. 1, 2022

(54) METHOD AND DEVICE FOR THE NON-INVASIVE INDIRECT IDENTIFICATION OF SITES OF ALTERATIONS OF THE BLOOD-RETINAL BARRIER

(71) Applicant: AIBILI-ASSOCIAÇÃO PARA INVESTIGAÇÃO BIOMÉDICA E INOVAÇÃO EM LUZ E IMAGEM, Coimbra (PT)

(72) Inventors: José Guilherme Fernandes Da Cunha-Vaz, Coimbra (PT); Torcato Miguel Barreira Paredes Dos Santos, Coimbra (PT)

(73) Assignee: AIBILI-ASSOCIAÇÃO PARA INVESTIGAÇÃO BIOMÉDICA E INOVAÇÃO EM LUZ E IMAGEM, Coimbra (PT)

( * ) Notice: Subject to any disclaimer, the term of this patent is extended or adjusted under 35 U.S.C. 154(b) by 217 days.

(21) Appl. No.: 15/568,161
(22) PCT Filed: Apr. 29, 2016
(86) PCT No.: PCT/IB2016/052462
§ 371 (c)(1),
(2) Date: Oct. 20, 2017
(87) PCT Pub. No.: WO2016/174637
PCT Pub. Date: Nov. 3, 2016

(65) Prior Publication Data
US 2018/0146850 A1 May 31, 2018

Related U.S. Application Data
(63) Continuation-in-part of application No. PCT/IB2015/060078, filed on Dec. 31, 2015.

(30) Foreign Application Priority Data

| Apr. 29, 2015 | (PT) | ......... 108418 |
| Sep. 10, 2015 | (PT) | ......... 108812 |
| Dec. 10, 2015 | (PT) | ......... 109028 |

(51) Int. Cl.
| A61B 3/10 | (2006.01) |
| A61B 3/12 | (2006.01) |
| G06T 7/00 | (2017.01) |

(52) U.S. Cl.
CPC ........... *A61B 3/102* (2013.01); *A61B 3/1225* (2013.01); *G06T 7/0012* (2013.01); *G06T 2207/10101* (2013.01); *G06T 2207/30041* (2013.01)

(58) Field of Classification Search
CPC ........... A61B 3/1225; A61B 3/14–158; A61B 3/0025; G06T 7/0012; G06T 2207/30041; G06T 2207/10101
(Continued)

(56) References Cited

U.S. PATENT DOCUMENTS

| 2007/0115481 A1* | 5/2007 | Toth ..................... A61B 3/0025 356/511 |
| 2012/0134563 A1* | 5/2012 | Nakano ................. G06T 7/0012 382/131 |

(Continued)

FOREIGN PATENT DOCUMENTS

| EP | 2458550 A2 | 5/2012 |
| WO | 2009149131 A1 | 12/2009 |
| WO | 2013022986 A1 | 2/2013 |

OTHER PUBLICATIONS

Fujimoto J., Drexler W. (2008) Introduction to Optical Coherence Tomography. In: Drexler W., Fujimoto J.G. (eds) Optical Coherence Tomography. Biological and Medical Physics, Biomedical Engineering. Springer, Berlin, Heidelberg, https://doi.org/10.1007/978-3-540-77550-8_1.*

(Continued)

*Primary Examiner* — Kristina M Deherrera
(74) *Attorney, Agent, or Firm* — Leason Ellis LLP

(57) ABSTRACT

Methods and devices for detecting sites of low optical reflectivity from optical coherence tomography, OCT, of the (Continued)

retina are provided. The method includes segmenting retinal layers from OCT data, calculating optical reflectivity of each segmented retinal layers from the OCT data, and detecting sites of low optical reflectivity from the calculated optical reflectivity of the segmented retinal layers. The calculated optical reflectivity can be compared against a predetermined threshold obtained from a healthy population. Segmenting can be carried out according to the optical reflectivity of each identified retinal layer. OCT-Microangiography data can be displayed side-by-side or superimposed with the enface images of the calculated optical reflectivity. The device can be combined with OCT equipment, in particular for displaying the detected sites of low optical reflectivity.

16 Claims, 31 Drawing Sheets

(58) Field of Classification Search
USPC .................................................. 351/206, 207
See application file for complete search history.

(56) References Cited

U.S. PATENT DOCUMENTS

| 2012/0150029 | A1* | 6/2012 | Debuc | G06T 7/12 |
| | | | | 600/425 |
| 2013/0286354 | A1 | 10/2013 | Stetson et al. | |
| 2016/0228000 | A1* | 8/2016 | Spaide | A61B 3/0025 |

OTHER PUBLICATIONS

Bandello et al. "Retinal layer location of increased retinal thickness in eyes with subclinical and clinical macular edema in diabetes type 2." Ophthalmic Research 54.3 (2015): 112-117.
Bernardes et al. "Noninvasive Evaluation of Retinal Leakage Using Optical Coherence Tomography." Ophthalmologica 2011; 226:29-36. 22 pages. https://doi.org/10.1159/000326268.
Bernardes et al. "Evaluation of Blood-Retinal Barrier Function from Fourier Domain High-Definition Optical Coherence Tomography." IFMBE Proceedings World Congress on Medical Physics and Biomedical Engineering, Sep. 7-12, 2009, Munich, Germany, 2009, 8 pages. doi:10.1007/978-3-642-03891-4_84.
Cunha-Vaz et al. "Early breakdown of the blood-retinal barrier in diabetes." British Journal of Ophthalmology 59 11 [1975]: 649-656.
Cunha-Vaz et al. "Blood-retinal barrier." European Journal of Ophthalmology 21 (2011): S3-9.
Debuc. "A review of algorithms for segmentation of retinal image data using optical coherence tomography." Image Segmentation. InTech, 2011. 41 pages.
Francis et al. "Enface thickness mapping and reflectance imaging of retinal layers in diabetic retinopathy." PloS one 10.12 (2015): e0145628. 16 pages. Doi10.1371/journal.pone.0145628.
Garvin et al. "Intraretinal layer segmentation of macular optical coherence tomography images using optimal 3-D graph search." IEEE Transactions on Medical Imaging 27.10 (2008): 1495-1505. 26 pages.
Horii et al. "Fluorescein Intensity of Cystoid Spaces is Negatively Correlated to Optical Coherence Tomographic Reflectivity in Diabetic Macular Edema." Investigative Ophthalmology & Visual Science 52.14 (2011): 568-568.
Horii et al. "Relationship between fluorescein pooling and optical coherence tomographic reflectivity of cystoid spaces in diabetic macular edema." Ophthalmology 119.5 (2012): 1047-1055.
International Search Report for International Patent Application No. PCT/IB2016/052462 dated Aug. 5, 2016. 4 pages.
Jia et al. "Quantitative optical coherence tomography angiography of vascular abnormalities in the living human eye." Proceedings of the National Academy of Sciences 112.18 (2015): E2395-E2402. 8 pages.
Li et al. "Optimal surface segmentation in volumetric images—a graph-theoretic approach." IEEE Transactions on Pattern Analysis and Machine Intelligence 28.1 (2006): 119-134. 39 pages.
Neubauer et al. "Topography of diabetic macular oedema compared with fluorescein angiography." Acta Ophthalmologica 85.1 (2007): 32-39.
Santos et al. "Feasibility of automated interface segmentation of Cirrus HD-OCT data in normal and mild non proliferative diabetic retinopathy eyes." Investigative Ophthalmology & Visual Science 56.7 (2015): 5953-5953.
Yannuzi et al. "Fluorescein angiography complication survey." Ophthalmology 93.5 (1986): 611-617.

* cited by examiner

METHOD AND DEVICE FOR THE NON-INVASIVE INDIRECT IDENTIFICATION OF SITES OF ALTERATIONS OF THE BLOOD-RETINAL BARRIER

CROSS REFERENCE TO RELATED APPLICATIONS

This application is a U.S. National Stage Application under 35 U.S.C. § 371 of International Patent Application No. PCT/1132016/052462, filed Apr. 29, 2016, which claims priority to Portugal Application No. 108418, filed Apr. 29, 2015, Portugal Application No. 108812, filed Sep. 10, 2015, Portugal Application No. 109028, filed Dec. 10, 2015, and International Patent Application No. PCT/1132015/060078, filed Dec. 31, 2015, which are hereby incorporated by reference in their respective entireties.

TECHNICAL FIELD

The present disclosure relates to a method and device for the non-invasive indirect identification of the sites of alterations of the Blood-Retinal Barrier, in particular it relates to the automated analysis of retinal extracellular space using Optical Coherence Tomography.

BACKGROUND

According to the International Diabetes Federation, the number of people with diabetes will rise from 387 million (in 2014) to 592 million (in 2035), worldwide, representing a prevalence of 8.3% and 11.3%, respectively.

Diabetes Mellitus (DM) is one of the most frequent diseases in clinical practice and both the prevalence and incidence of this multifactorial disease have shown an increase in recent years. Diabetic retinopathy (DR) is also a frequent complication of DM and is the main cause of vision loss in the active working population in western countries, being responsible for 10% of the new case of blindness each year [1].

In DR, the blood-retinal barrier (BRB) has been shown to be altered since the initial stages of DR [1]. Similarly, other retinal vascular diseases are directly associated with an alteration of the BRB.

In the healthy retina, the BRB, structurally based on the tight junctions of the retinal pigment epithelium (RPE) and the tight junctions of the endothelial cells of the capillary network, prevent fluid diffusion into the retina and vitreous. Fluorescein angiography (FA) is the imaging technique most frequently used to document the changes occurring in the BRB in DR. It uses sodium fluorescein (NaFl) as a dye and images are acquired after intravenous administration. Because of the intravenous dye administration, minor adverse reactions occur in 5% of the cases. Severe complications, although more rare, may occur, the reason why this imaging technique requires the presence of a MD. Death may still occur in the first 24 to 48 hours for each 220.000 cases [2].

Recently, Optical Coherence Tomography (OCT) Microangiography has been introduced for non-invasive vascular imaging in the eye. It replaces FA by identifying non-invasively neovascularization and is capable of quantifying capillary dropout in the retinal circulation, but it does not identify sites of leakage, i.e., alteration of BRB. Thus far, there has been no method proposed to image leakage or breakdown of BRB [3].

It is thus desirable to obtain non-invasive imaging techniques for identifying the location and measuring extracellular space increases which are surrogate indicators of alteration of the BRB, i.e., to complement the already available OCT-Microangiography and, therefore, to fully replace the need for FA.

The following documents are herewith expressly incorporated by reference.
1. Cunha-Vaz J G, Faria de Abreu J R, Campos A J, Figo G. Early breakdown of the blood-retinal barrier in diabetes. Br J Ophthalmol 1975; 59:649-656.
2. Yannuzi L A, Rohrer K T, Tindel L J, Sobel R S, Constanza M A, Shields W, Zang E. Fluorescein angiography complications survey. Ophthalmology 1986; 93:611-617.
3. Jia Y, Bailey S T, Hwang T S, McClintic S M, Gao S S, Pennesi M E, Flaxel C J, Lauer A K, Wilson D J, Hornegger J, Fujimoto J G, Huang D. Quantitative optical coherence angiography of vascular abnormalities in the living human eye. Proc Natl Acad Sic 2015; 112(18): E2395-402.
4. Li K., Wu X., Chen D., Sonka M. Optimal Surface Segmentation in Volumetric Images—A Graph-Theoretic Approach. IEEE Trans Pattern Analysis and Machine Intelligence 2006; 28(1):119-134.
5. Garvin M K, Abramoff M D, Kardon R, Russel S R, Wu X, Sonka M. Intraretinal layer segmentation of macular optical coherence tomography images using optimal 3-D graph search. IEEE Trans Med Imaging 2008; 27:1495-505.
6. Santos T, Correia A, Neves C, Schwartz C, Miranda T, Santos A, Cunha-Vaz J. Feasibility of automated interface segmentation of Cirrus HD-OCT data in normal and mild non proliferative diabetic retinopathy eyes. ARVO 2015 Annual Meeting, May 7th, Denver, Colo., USA. Invest Ophtalmol Vis Sci 2015; 56(7):5953.
7. Bandello F, Tejerina A, Vujosevic S, Varano M, Egan C, Sivaprasad S, et al. Retinal layer location of increased retinal thickness in eyes with subclinical and clinical macular edema in diabetes type 2. Ophthalmic Res. 2015; 54(3):112-117.

These facts are disclosed in order to illustrate the technical problem addressed by the present disclosure.

General Description

The present disclosure relates to a method and device for the non-invasive indirect identification of the sites of alterations of the Blood-Retinal Barrier, herewith optionally mentioned as OCT-Leakage, in particular it relates to the automated analysis of retinal extracellular space using Optical Coherence Tomography.

The disclosure presents a practical and efficient approach, being a robust rapid method to detect retinal alterations, able to produce images that are easier and simpler to interpret by an OCT operator. In particular, the disclosure when coupled to a suitable layer segmentation of the retina produces images that are particularly evident of retinal alteration.

Throughout the description and claims the word "comprise" and variations of the word, are not intended to exclude other technical features, additives, components, or steps. Additional objects, advantages and features of the disclosure will become apparent to those skilled in the art upon examination of the description or may be learned by practice of the disclosure. The following examples and drawings are provided by way of illustration, and they are not intended to be limiting of the present disclosure. Furthermore, the present disclosure covers all possible combinations of particular and preferred embodiments described herein.

The disclosure includes a method for detecting sites of low optical reflectivity from optical coherence tomography, OCT, of the retina comprising the steps of:
- segmenting retinal layers from OCT data;
- calculating the optical reflectivity of each of the segmented retinal layers from the OCT data;
- detecting sites of low optical reflectivity from the calculated optical reflectivity of the segmented retinal layers.

In an embodiment, detecting sites of low optical reflectivity comprises comparing the calculated optical reflectivity of the segmented retinal layers against a threshold.

In an embodiment, the threshold is predetermined.

In an embodiment, the threshold is predetermined according to the optical reflectivity of the segmented retinal layers from a healthy population.

In an embodiment, the OCT data is OCT data from OCT A-Scans obtained at transverse locations across the eye.

In an embodiment, segmenting retinal layers from OCT data comprises segmenting according to the optical reflectivity of each identified retinal layer, in particular segmenting for similar optical reflectivity of each identified retinal layer. Optionally, only a subset of all segmented layers need to be used for calculating the optical reflectivity and detecting sites of low optical reflectivity. Optionally, some of the segmented layers may be merged before calculating the optical reflectivity and detecting sites of low optical reflectivity. Optionally, some of the segmented layers may be merged after calculating the optical reflectivity but before detecting sites of low optical reflectivity.

In an embodiment, segmenting retinal layers from OCT data comprises graph-theory segmentation.

In an embodiment, detecting sites of low optical reflectivity from the calculated optical reflectivity of the segmented retinal layers comprises morphologic image operations.

In an embodiment, the steps of the method are carried out pixel by pixel with enface images.

An embodiment comprises generating enface images of the optical reflectivity of each of the segmented retinal layers.

An embodiment comprises displaying said images by a computer display and/or storing said images in a data storage media.

An embodiment comprises displaying OCT-Microangiography data in the same computer display, in particular side-by-side or superimposed with the enface images of the optical reflectivity of each of the segmented retinal layers.

An embodiment comprises the previous step of carrying out an OCT of the retina for obtaining the OCT data.

An embodiment comprises segmenting 6 to 11 retinal layers, in particular 7 retinal layers.

In an embodiment, the method is for identifying abnormal increases of intercellular fluid or extracellular space in the retina.

In an embodiment, the method is for non-invasive identification of sites of alterations of the blood-retinal barrier.

The disclosure also includes non-transitory data storage media including program instructions for implementing a device for detecting sites of low optical reflectivity from optical coherence tomography, the program instructions including instructions executable to carry out any of the disclosed methods.

The disclosure also includes a device comprising said non-transitory data storage media and an electronic data processor.

The disclosure also includes a device for detecting sites of low optical reflectivity from optical coherence tomography, said device being configured to carry out any of the disclosed methods.

In an embodiment, the device comprises an OCT equipment, in particular further comprising a computer display for displaying the detected sites of low optical reflectivity.

The disclosure also includes a method for detecting sites of retinal alterations from optical coherence tomography, OCT, data of an eye, wherein said data comprises OCT A-scan data over an area of the eye and each OCT A-scan data comprises a series of reflectivity values along the depth direction of the OCT A-scan, said method comprising:
- detecting sites for each OCT A-Scan having a reflectivity value lower than a predetermined threshold;
- generating a two dimensional image of the detected sites.

The disclosure also includes a method for detecting sites of retinal alterations from optical coherence tomography, OCT, data of an eye, wherein said data comprises OCT A-scan data over an area of the eye and each OCT A-scan data comprises a series of reflectivity values along the depth direction of the OCT A-scan, said method comprising:
- segmenting the OCT A-scan data into retinal layers;
- detecting sites for each retinal layer of each OCT A-Scan having a reflectivity value lower than a predetermined threshold;
- for each retinal layer, generating a two dimensional image of the detected sites.

The disclosure also includes a method for measuring extracellular fluid distribution from optical coherence tomography, OCT, data of an eye, wherein said data comprises OCT A-scan data over an area of the eye and each OCT A-scan data comprises a series of reflectivity values along the depth direction of the OCT A-scan, said method comprising:
calculating the ratio between
the number of OCT A-Scans with one or more reflectivity values below the predetermined threshold,
and the total number of OCT A-Scans within said area of the eye.

In an embodiment, the threshold is predetermined according to the optical reflectivity of a healthy population.

A threshold value can be established from the optical reflectivity of A-Scans from a series of healthy control eyes. The specific threshold value is established for the OCT device used, as it is dependent on the equipment. As an example, the predetermined threshold may be 20 when measured using an ANGIOPLEX™ OCT (angiography tool) or may be 10 when measured using an CIRRUS™ HD-OCT 5000 (optical coherence tomography tool).

In an embodiment, the method comprises previously obtaining OCT A-scans over an area of the eye, each A-scan comprising a series of reflectivity values along the depth direction of the scan.

In an embodiment, the method further comprising preprocessing the OCT A-scan data, said preprocessing comprising one or more of speckle reduction or normalization operations.

In an embodiment, the method is used for identifying increases of intercellular fluid or increases of extracellular space in the retina or alterations of the blood-retinal barrier.

In an embodiment, the method is used for identifying sites of alterations of the blood-retinal barrier.

The disclosure also includes a method to analyze optical coherence tomography (OCT) data of an eye comprising:

a) obtaining OCT A-scans over an area of the eye, each A-scan comprising a series of reflectivity values along the depth direction of the scan;
b) generating a two dimensional image of the area of the eye by assigning a single representative value for each A-scan;
c) identifying one or more locations of A-scans having reflectivity values falling below a predefined threshold (or predetermine threshold) in the two dimensional image; and
d) storing or displaying the two dimensional image or a further analysis thereof.

In an embodiment, the method further comprising segmenting the plurality of A-scans to identify different retinal layers along the depth direction of the A-scan.

In an embodiment, the method the reflectivity values in each retinal layer are analyzed separately.

In an embodiment, the predefined threshold is 20 when measured using an ANGIOPLEX™ OCT (angiography tool) or is 10 when measured using an CIRRUS™ HD-OCT 5000 (optical coherence tomography tool).

In an embodiment, the method is used to identify increases in the retinal extracellular space.

In an embodiment, the method comprises preprocessing the OCT A-scans prior to the steps (b), (c) and (d), said preprocessing comprising one or more of speckle reduction or normalization.

In an embodiment, the single representative value is one of the average of the reflectivity values of the A-scan, the median reflectivity value of the A-scan, the minimum reflectivity value of the A-scan, or the maximum reflectivity value in the A-scan.

In an embodiment, the step (b) includes normalizing the reflectivity to a known structure such as the retinal nerve fiber layer.

The disclosure also includes, a method to analyze optical coherence tomography (OCT) data of an eye comprising:
a) obtaining OCT A-scans over an area of the eye, each A-scan comprising a series of reflectivity values along the depth direction of the scan;
b) dividing each A-scan into multiple subsections along the depth direction of the scan;
c) generating one or more two dimensional images of the area of the eye by assigning a single representative value for the reflectivity values in the one or more subsections for each A-scan;
d) identifying locations of A-scans having reflectivity values falling below a predefined threshold in the two dimensional image for a particular subsection; and
e) storing or displaying the two dimensional image or a further analysis thereof.

In an embodiment, the multiple subsections represent different retinal layers in the eye.

BRIEF DESCRIPTION OF THE DRAWINGS

The following figures provide preferred embodiments for illustrating the description and should not be seen as limiting the scope of invention.

FIG. 1A: Full length SD-OCT A-Scan from a healthy subject. FIGS. 1B-1C: Detail of SD-OCT A-Scan in the retina for a healthy subject (FIG. 1B) and for a NPDR patient with CME (FIG. 1C). SD-OCT A-Scan optical reflectivity from each of the segmented layers are differentiated. Optical reflectivity threshold is shown in a dashed horizontal line. Vertical lines indicate the limits of the retina.

FIG. 4A: FA image at 5 minutes and seven seconds after injection with localized leakage in the nasal inner ring. FIG. 4B: OCT-Leakage map of the full retina scan showing increased extracellular space in the same location of the FA leakage. FIG. 4C: OCT RT map (CIRRUS™ HD-OCT 5000 [optical coherence tomography tool], Zeiss). FIG. 4D: B-Scan centered on the fovea. FIGS. 4E-4J: OCT-Leakage maps of the different retinal layers showing higher LOR ratios corresponding to increased extracellular space on the OPL and extending to the IS+OS layer.

It can be clearly seen how the layer discrimination emphasizes the relevant LOR information—see FIG. 4G and to some extent FIG. 4I—while the full retina scan in FIG. 4B "hides" said information in what can be termed "noise". FIG. 4G correlates very well with FIG. 4A, demonstrating the effect and usefulness of the current disclosure.

FIG. 5A: an area of late fluorescein leakage is well identified five minutes and one second after injection. FIG. 5B: OCT-Leakage map of the full retina scan showing increase in the extracellular space in the same topographical location. FIG. 5C: OCT RT map (CIRRUS™ HD-OCT 5000 [optical coherence tomography tool], Zeiss), showing abnormal RT in the central subfield. FIG. 5D: B-Scan centered on the fovea. FIGS. 5E-5J: OCT-Leakage maps of the different retinal layers showing localized accumulation of fluid in the INL in the location corresponding to the site of late leakage on FA. There is also increase in extracellular space in the ONL in the same area.

Figure 5B:
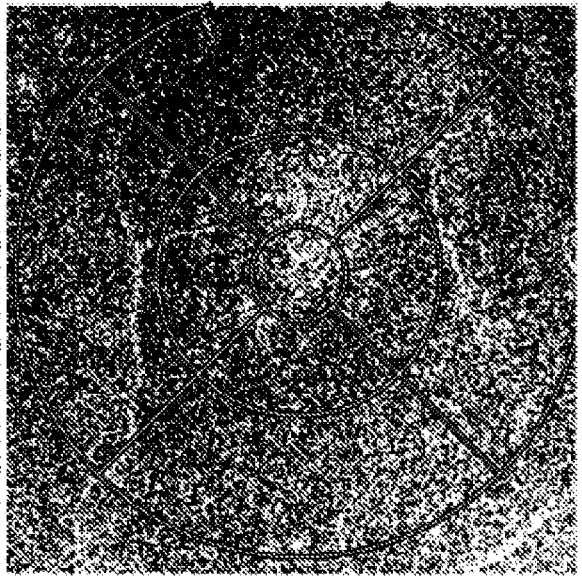
FIGS. 5A-5J—Eye with diabetic CME and localized fluorescein leakage on FA.
Figure 5A:
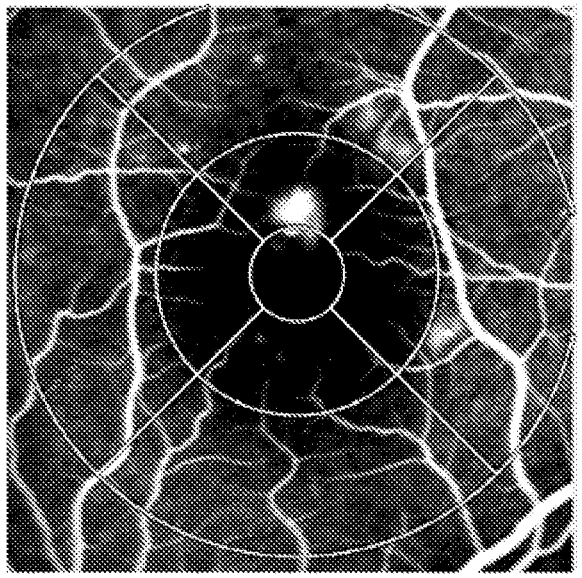
Figure 5D:
Figure 5C:
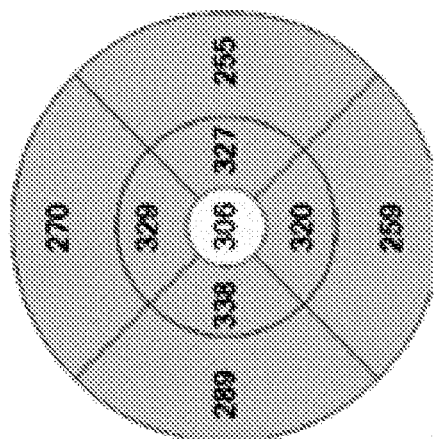
Figure 5F:
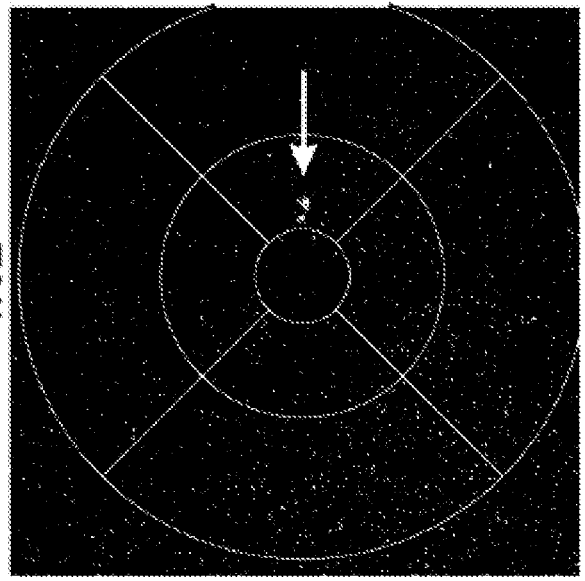
Figure 5E:
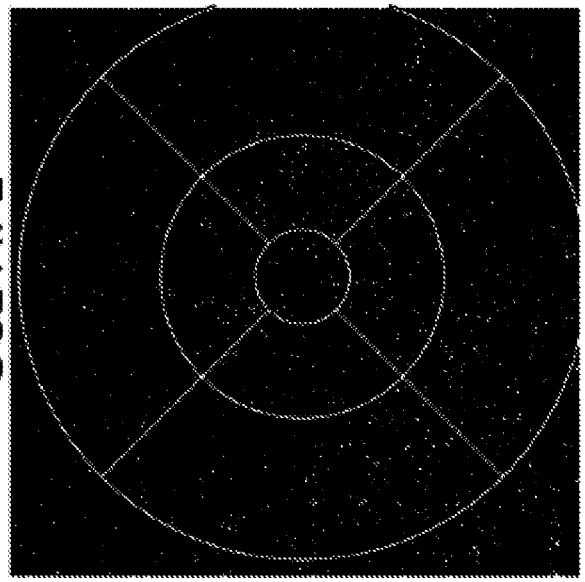
Figure 5H:
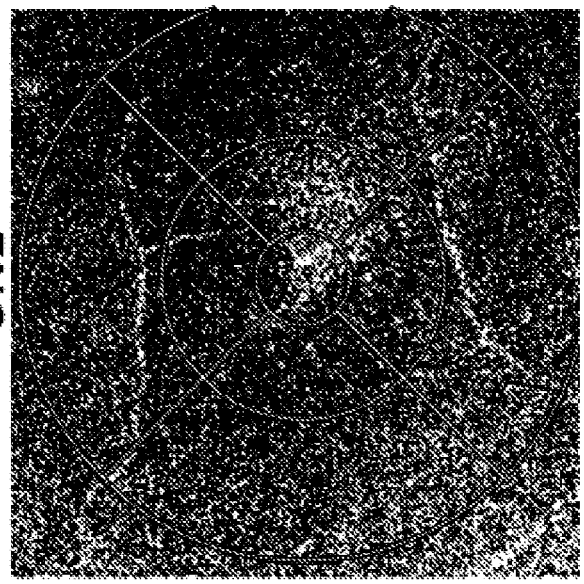
Figure 5G:
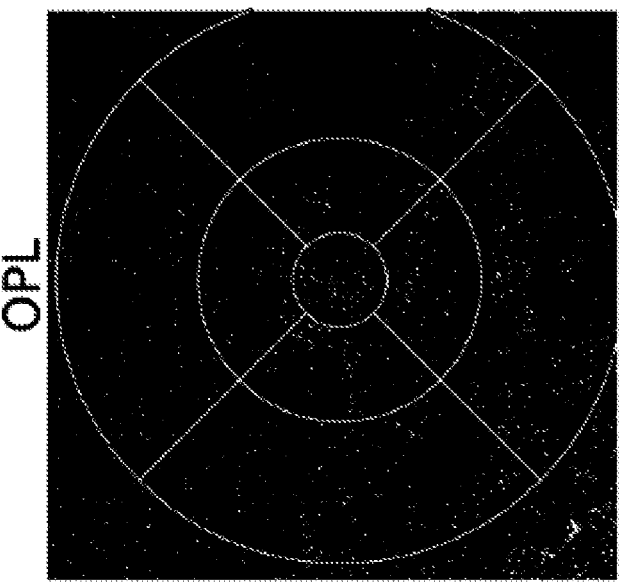
Figure 5J:
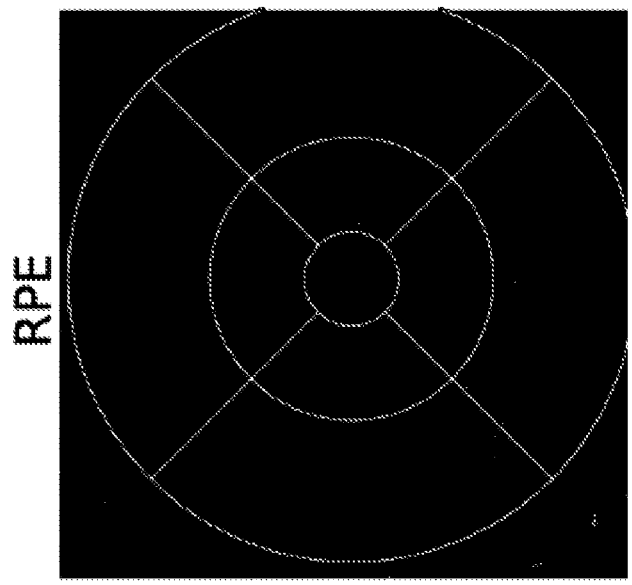
Figure 5I:
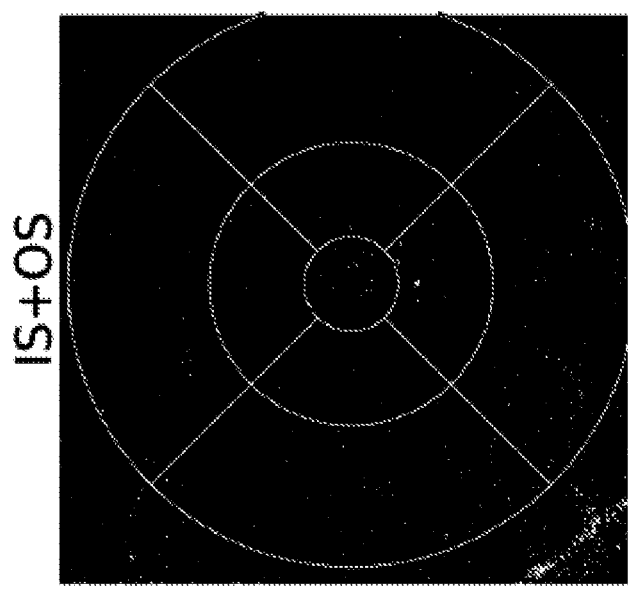

Again, the layer discrimination of the LOR data is a powerful tool for clearly pointing out locations having an increase in the extracellular space—see FIG. 5F.

Figure 6B:
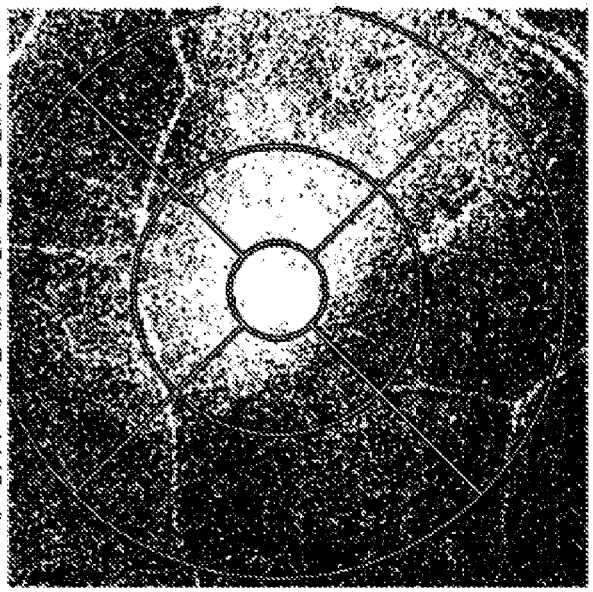
Figure 6A:
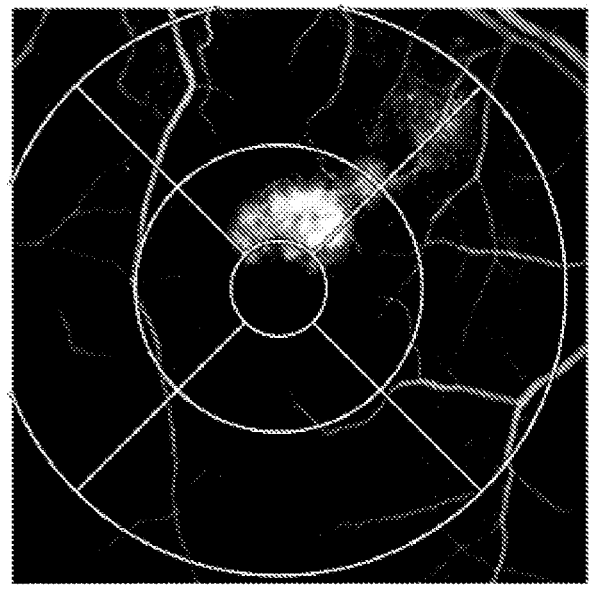
Figure 6C:
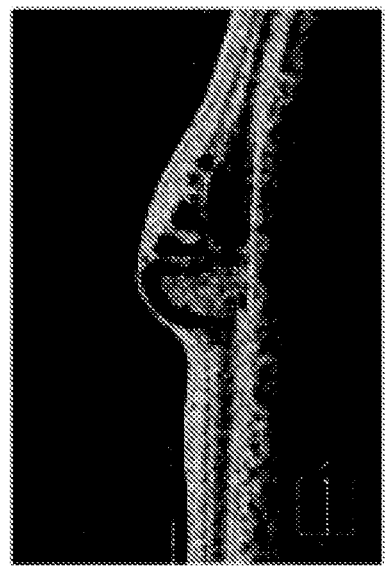
Figure 6D:
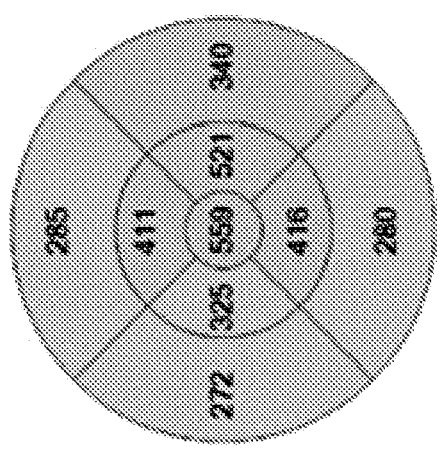
Figure 6F:
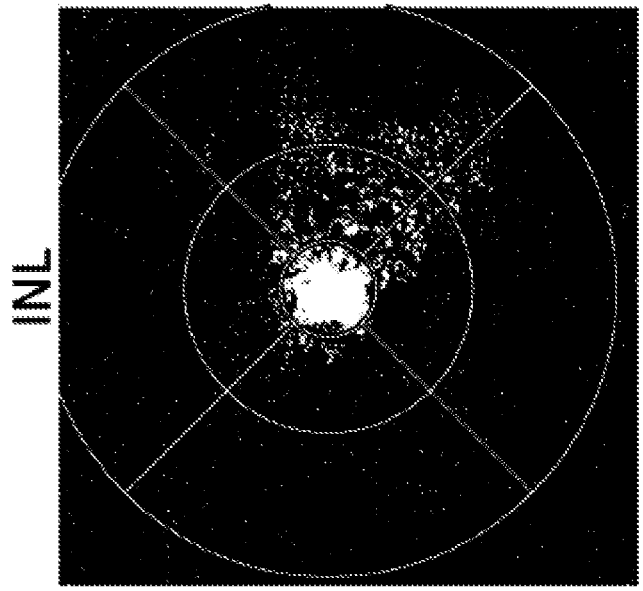
Figure 6E:
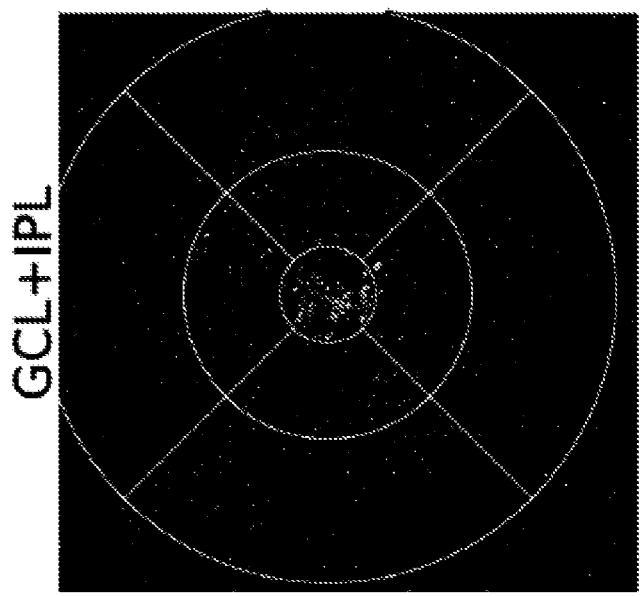
Figure 6H:
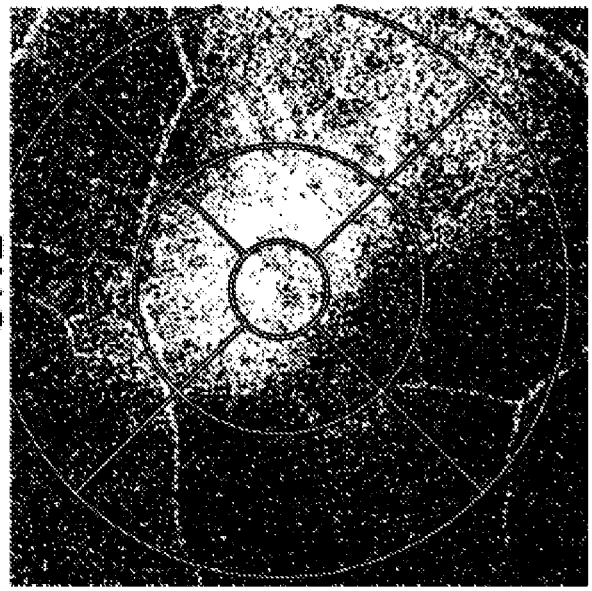
Figure 6G:
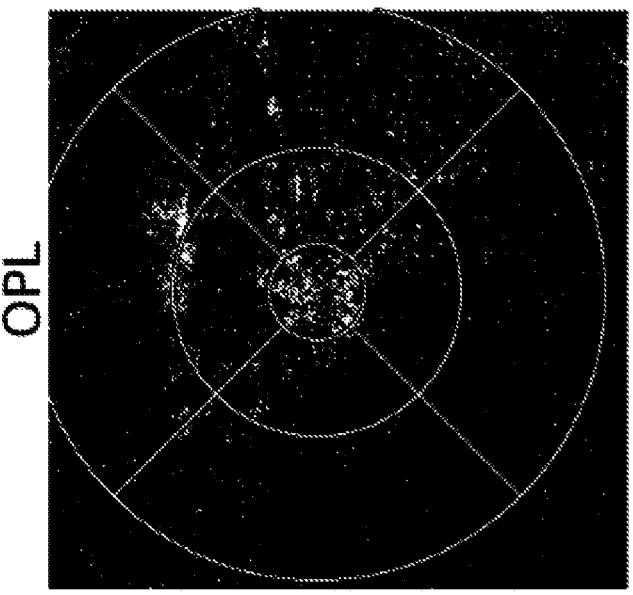
Figure 6J:
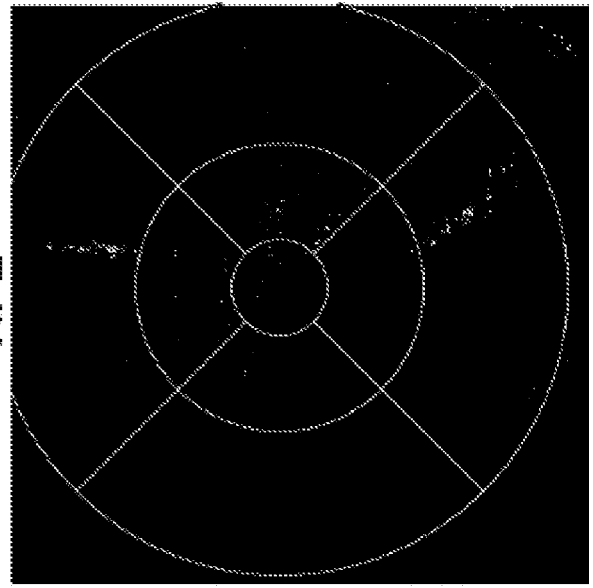
Figure 6I:
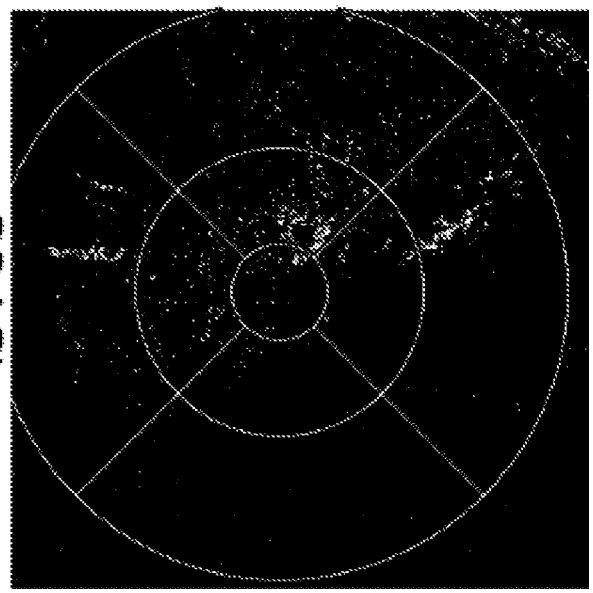

FIGS. 6A-6J—Eye with branch retinal vein occlusion and evidence of fluorescein leakage on FA. FIG. 6A: a well-defined localized leakage spot on FA, five minutes and thirty nine seconds after injection, mainly located in the nasal inner ring. FIG. 6B: OCT-Leakage map of the full retina scan showing increased extracellular space in the same location of the FA leakage but showing also clear involvement of the central subfield. FIG. 6C: OCT RT map (CIRRUS™ HD-OCT 5000 [optical coherence tomography tool], Zeiss). FIG. 6D: B-Scan centered on the fovea. FIGS. 6E-6J: OCT-Leakage maps of the different retinal layers showing higher LOR ratios corresponding to increased extracellular space in the INL, OPL, ONL and extending to the IS+OS layer.

Again, the layer discrimination of the LOR data enhances the information obtained from the OCT.

Figures 7A, 7B:
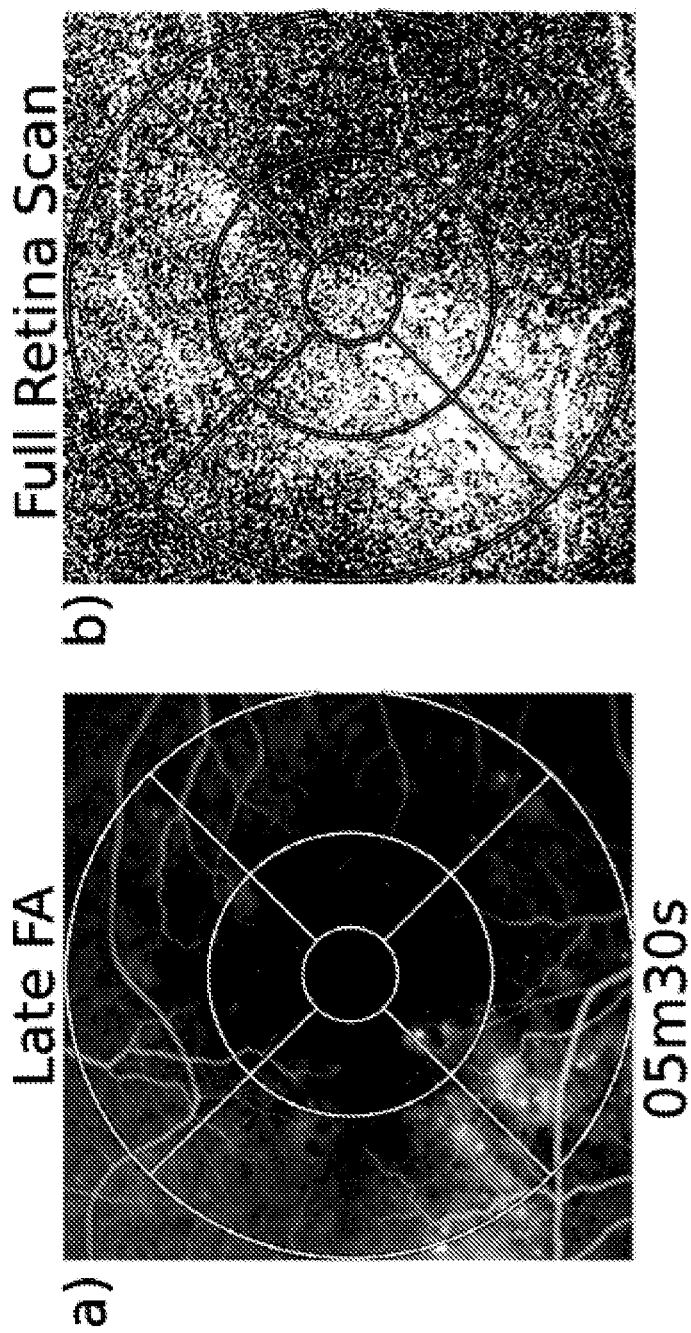
Figure 7D:
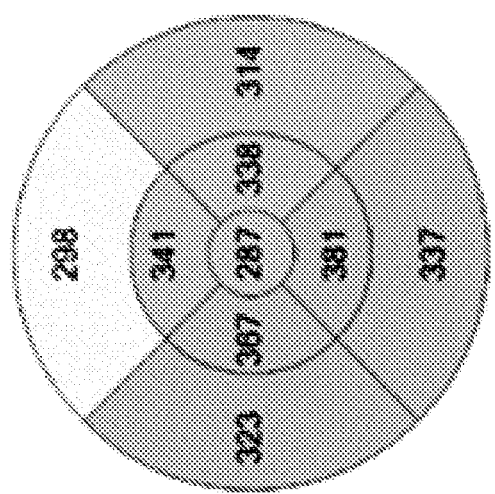
Figure 7C:
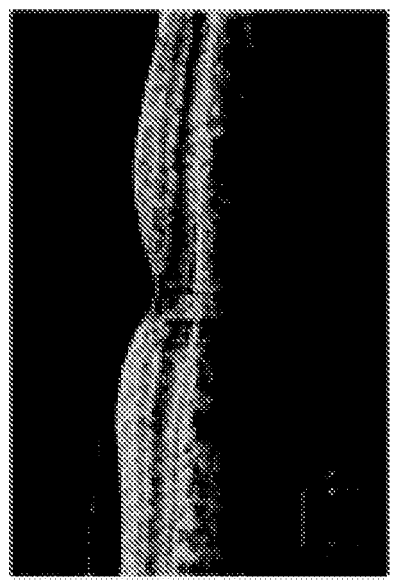
Figure 7F:
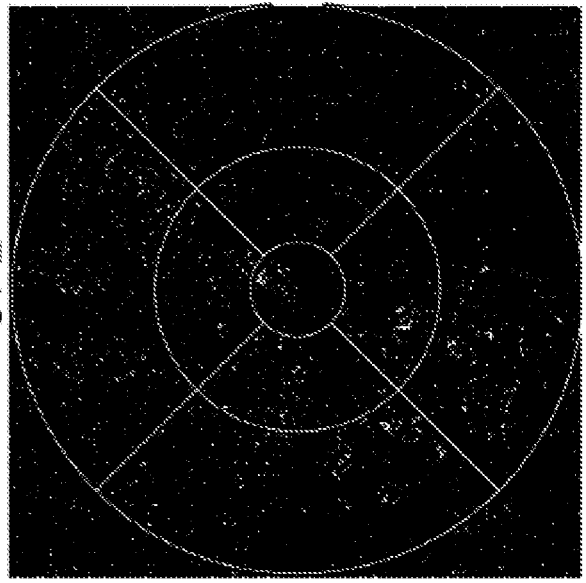
Figure 7E:
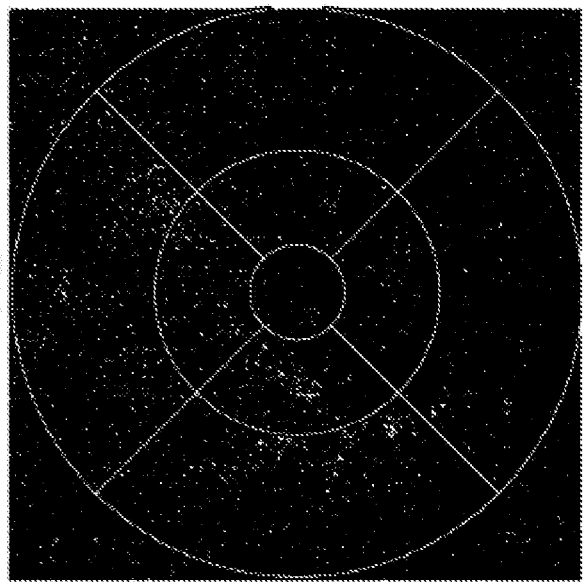
Figure 7H:
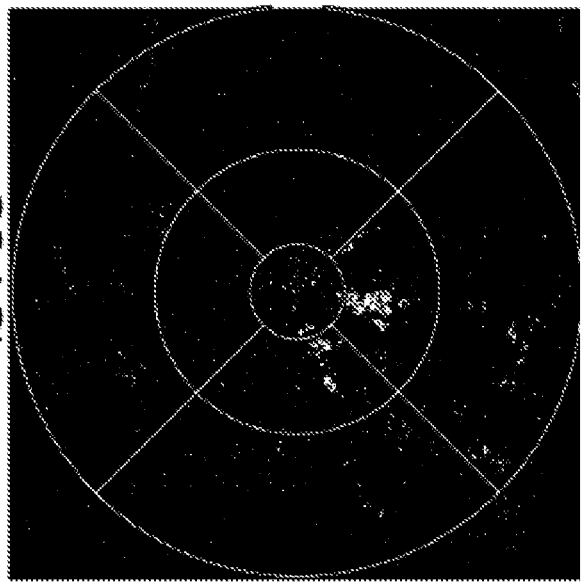
Figure 7G:
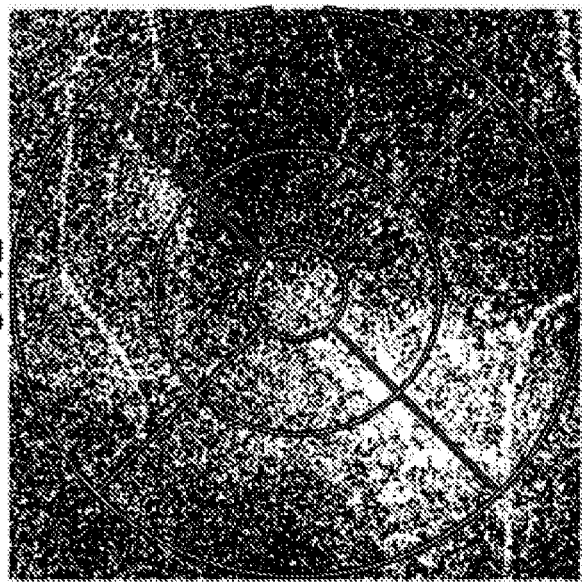
Figure 7I:
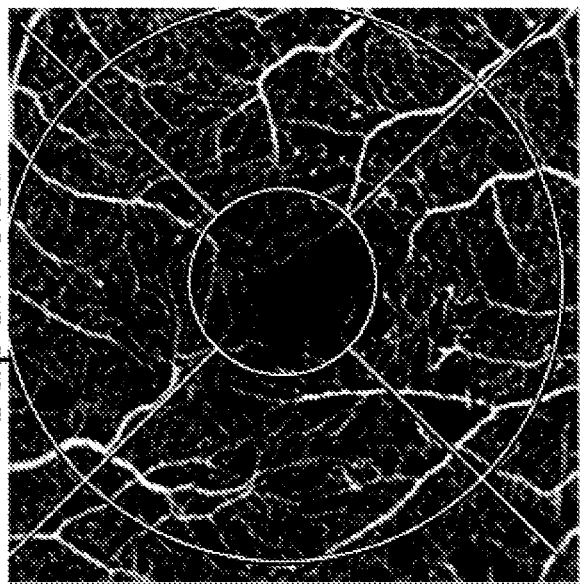
Figure 7J:
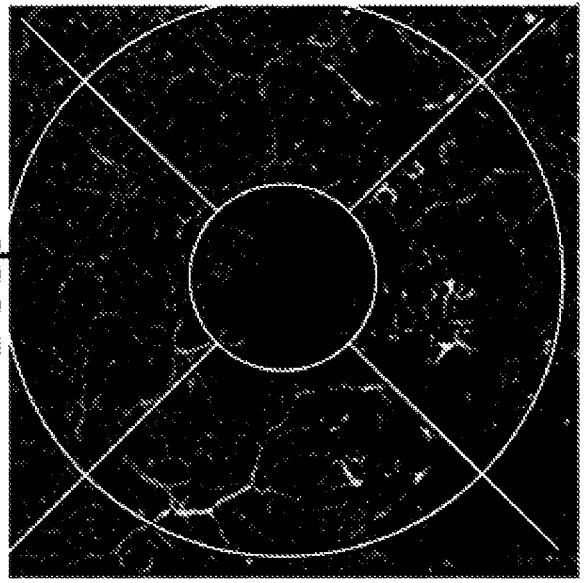

FIGS. 7A-7J—Eye with diabetic CME and evidence of localized fluorescein leakage on FA, corresponding well with increase in extracellular space detected in the OCT-Leakage. FIG. 7A: an area of late fluorescein leakage five minutes and thirty seconds after injection. FIG. 7B: OCT-Leakage map of the full retina scan showing abnormal increase of the extracellular space in the same topographic location. FIG. 7C: OCT RT maps (CIRRUS™ HD-OCT 5000 [optical coherence tomography tool], Zeiss) with RT increase in inferior and temporal inner outer rings. FIG. 7D: B-Scan centered on the fovea. FIGS. 7E-7H: OCT-Leakage maps of different retinal layers showing localized accumulation of fluid in the locations corresponding to the site of late leakage on FA. FIGS. 7I and 7J: complementary images of the superficial and deep vascular nets obtained with ANGIOPLEX™ OCT (angiography tool) showing signs of interruption of macular capillaries.

Again, the layer discrimination of the LOR data enhances the information obtained from the OCT, being less sensitive to the image interferences caused by blood vessels—see for example FIG. 7H.

DETAILED DESCRIPTION

In order to demonstrate the effect and usefulness of the disclosure, a study of exploratory analysis of eyes/patients, in the context of a prospective, multicenter, observational study was designed to follow eyes/patients with mild non-proliferative diabetic retinopathy (NPDR)—20 and 35 of the Early Treatment Diabetic Retinopathy Study (ETDRS) classification.

All patients included with CIRRUS™ HD-OCT 5000 (optical coherence tomography tool) signal strength equal or greater than 7 and with a successful automatic segmentation were included in the analysis. Following reference values by DRCR.net for retinal thickness (RT) in the central subfield we examined 10 eyes from 10 diabetic patients between 50 and 72 years of age (m±sd: 61.20±7.52 [years]) with normal RT, 30 eyes from 30 diabetic patients between 48 and 82 years of age (m±sd: 60.97±7.80 [years]) with Subclinical Macular Edema (SME) and 8 eyes from 8 diabetic patients between 43 and 73 years of age (m±sd: 62.25±9.73 [years]) with Clinical Macular Edema (CME). To serve as a control population, we included 25 eyes from 21 age matched patients from our healthy normative database, between 49 and 75 years of age (m±sd: 60.64±5.43 [years]).

In order to examine correlations between FA sites of fluorescein leakage and changes in retinal extracellular space detected by our technique of OCT-Leakage, we also examined the OCT data obtained from 2 eyes with SME and 8 CME eyes from 8 NPDR patients from 53 to 75 years of age, (m±sd: 61.88±6.73 [years]) with initial stages of diabetic retinal disease which had performed FA examinations. This later analysis was performed on patients, in the context of a prospective, observational study designed to characterize eyes/patients with DME that show different treatment responses to intravitreal anti-VEGF injections.

Finally, to test the application in eyes with different retinal diseases other than diabetes we examined also eyes with branch retinal vein occlusion, central serous chorioretinopathy and macular edema after cataract surgery. In these patients and in four of the patients with diabetes, OCT-Microangiography was also performed, in order to evaluate the complementarity of the information obtained by OCT-Microangiography and OCT-Leakage.

OCT scans the retina locations with a low coherence near-infra red light beam from a superluminescent diode to compute a retina profile by interferometry of the reflected light from the sample and reference arms. This axial retinal profile, named as A-Scan, is repeated on the next laterally adjacent retina location to produce a B-Scan which provides a high resolution cross-sectional image of the retina. The results here reported for Spectral Domain OCT use a CIRRUS™ HD-OCT 5000 (optical coherence tomography tool) (Carl Zeiss Meditec, Dublin, Calif., USA) with an acquisition speed of 27 000 A-Scans per second to image a 6×6×2 mm3 volume of the retina by 512×128×1024 voxels with 5 μm axial and 20 μm lateral resolutions.

OCT microangiograms were acquired with ANGIOPLEX™ OCT (angiography tool) Angiography (Carl Zeiss Meditec, Dublin, Calif., USA). This system uses of a light source centered at 840 nm with a 50 nm bandwidth, providing a 5 um axial resolution in tissue. With a acquisition speed of 27 000 A-Scans per second, we were able to scan the 6×6×2 mm2 or 3×3×2 mm2 of retinal volume by 350×350×1024 or 245×245×1024 voxels respectively.

For retinal layer segmentation, an in-house graph-theory segmentation algorithm from Li et al. and Garvin et al. [4,5], suitably adapted, was implemented to automatically identify 7 retinal layers namely the Retinal Nerve Fiber Layer (RNFL), Ganglion Cell and Inner Plexiform Layers (GCL+IPL), Inner Nuclear Layer (INL), Outer Plexiform Layer (OPL), Outer Nuclear Layer (ONL), Inner and Outer Segment (IS+OS) and the Retinal Pigment Epithelium (RPE). Results from the segmentation algorithm results were validated by one grader and local corrections were performed as needed [6,7]. Root mean square errors (RMSE) between automatic and human grader segmentations for healthy subjects and for diabetic patients are of the same order of magnitude. Larger RMSE were found at OS/RPE interface ranging from 3.97 to 16.61 μm (m±sd: 6.92±2.21 μm) and from 0.65 to 17.76 μm (m±sd: 4.24±2.69 μm) for healthy and diabetic patients, respectively.

FA, fluorescein angiography, was performed by the intravenous injection of 5 ml of fluorescein 10% dye into the antecubital vein. Photographs of the study eye are thereafter taken during the early transit phase from 15 to 45 seconds, at 60 to 90 seconds, and at 5 to 10 minutes.

As light from the OCT superluminescent light emitting diode operating at 840 nm is absorbed by hemoglobin, superficial vessels (larger caliber vessels) produce a shadowing effect into the deeper retina locations. Also taking into account the OCT high reflectivity intensities at the RPE layer, we were able to calculate a 2 dimensional enface OCT reference image which discriminates vessel locations from the remaining background. Pairs of points on vessel bifurcation in enface OCT and FA images were thereafter manually earmarked to be used as control points for the projective transformation calculation. This enabled us to accurately map the sites of fluorescein leakage on the FA image and to correlate their location with the OCT data.

Figure 1A:
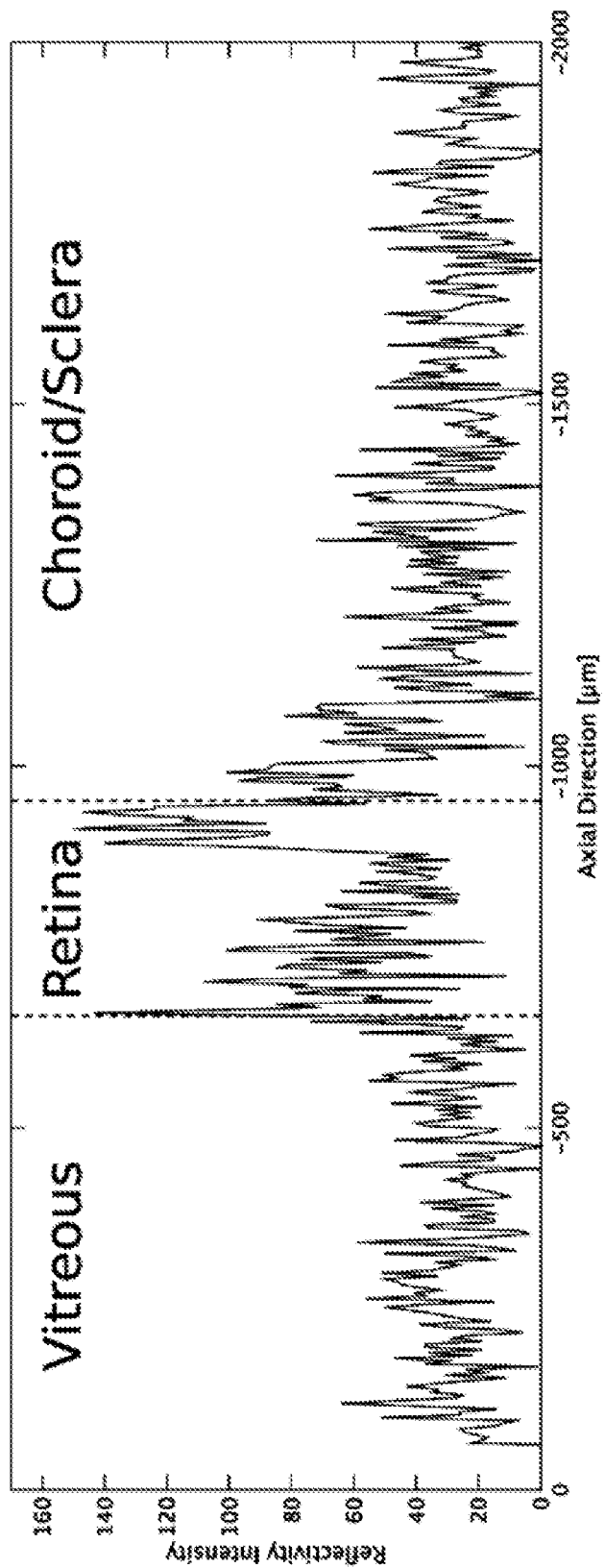
FIGS. 1A-1C—Cirrus SD-OCT A-Scan optical reflectivity profiles.
Figure 1B:
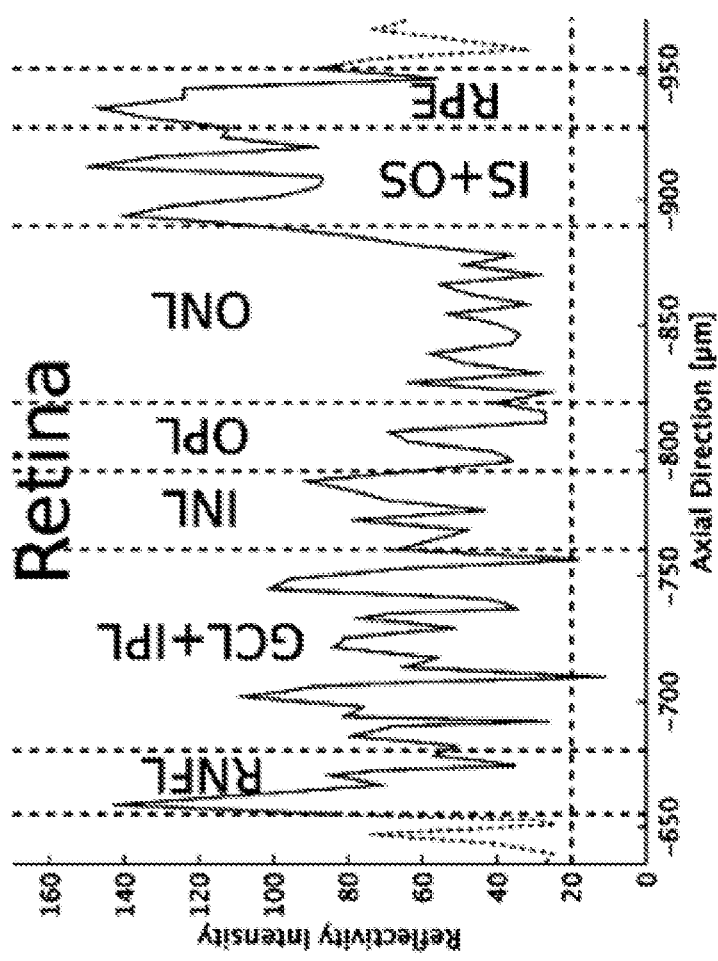
Figure 1C:
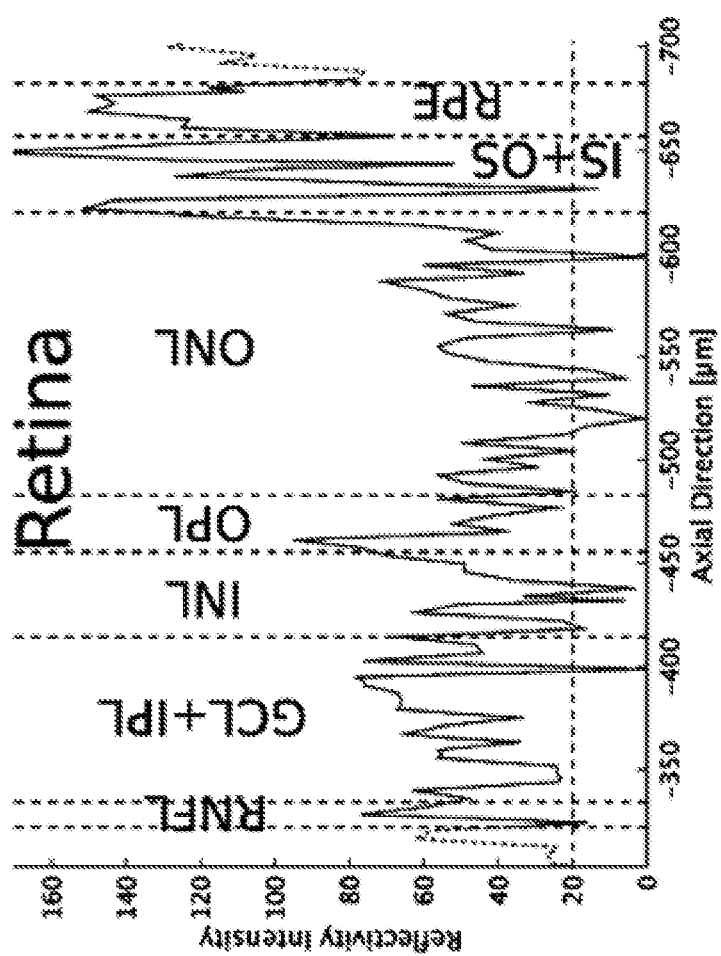
Figure 2B:
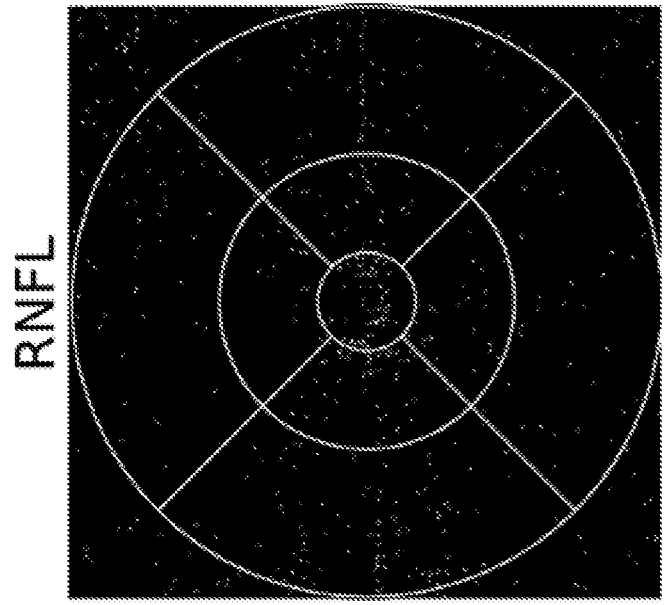
FIGS. 2A-2H—ANGIOPLEX™ OCT (angiography tool) Angiography LOR maps for the right eye of a healthy subject for the full retina scan and for each of the segmented retinal layers. The represented layers are full retina, RNFL, GCL+IPL, INL, OPL, ONL, IS+OS and RPE from FIGS. 2A-2H, respectively. Locations of low optical reflectivity are identified in white. The ETDRS grid is centered at the fovea.
Figure 2A:
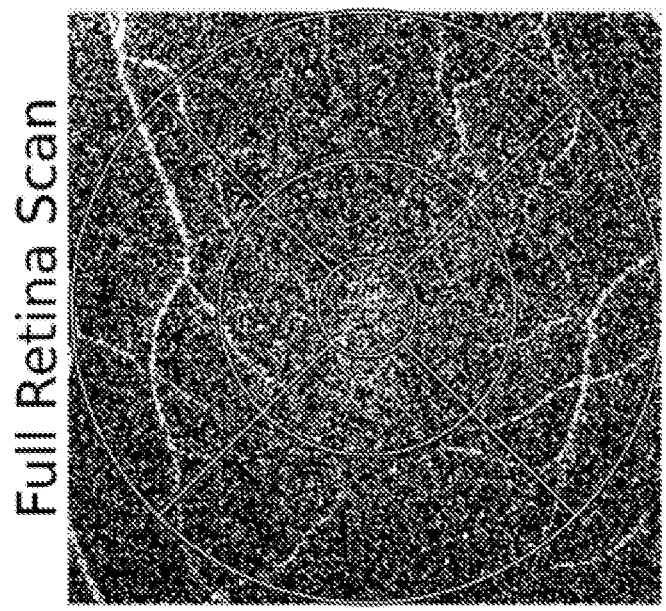
Figure 2D:
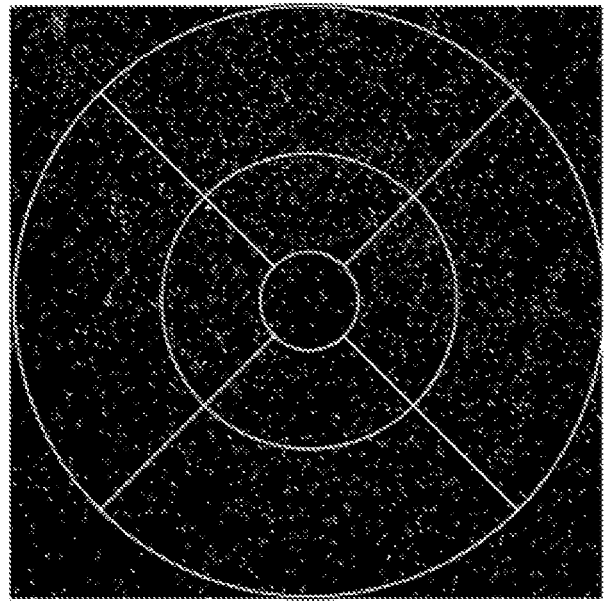
Figure 2C:
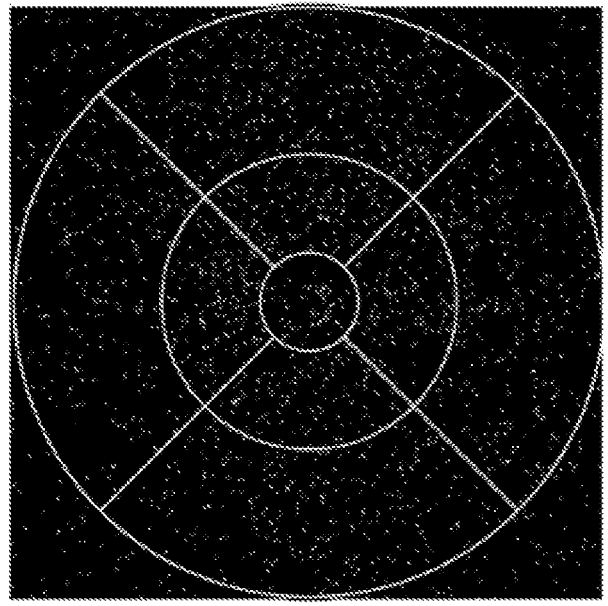
Figure 2F:
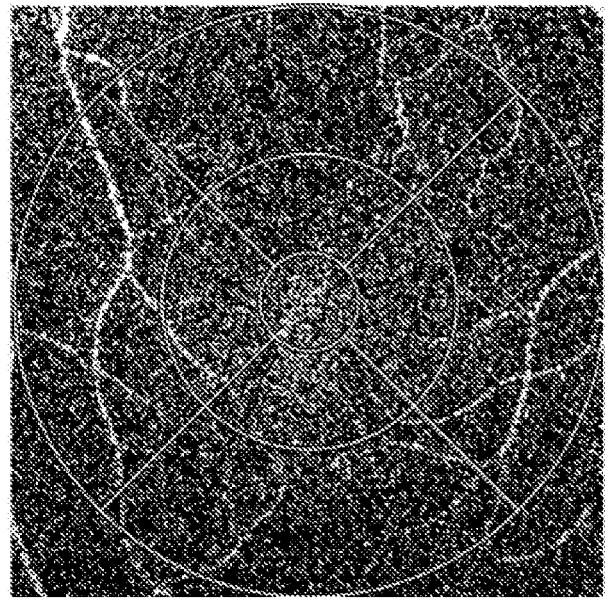
Figure 2E:
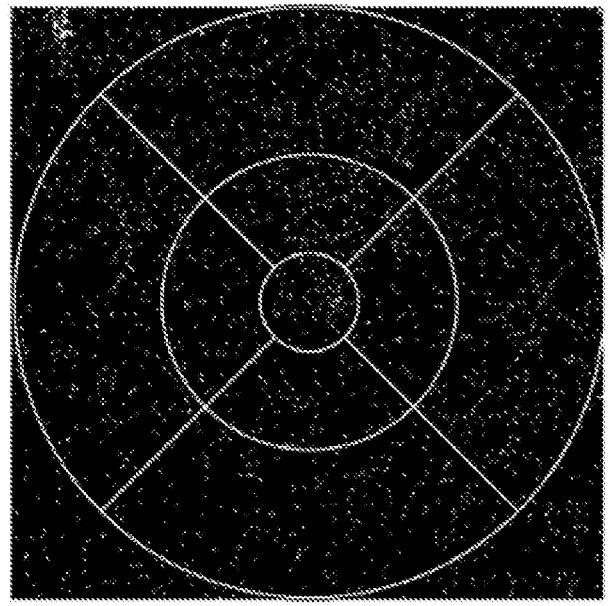
Figure 2H:
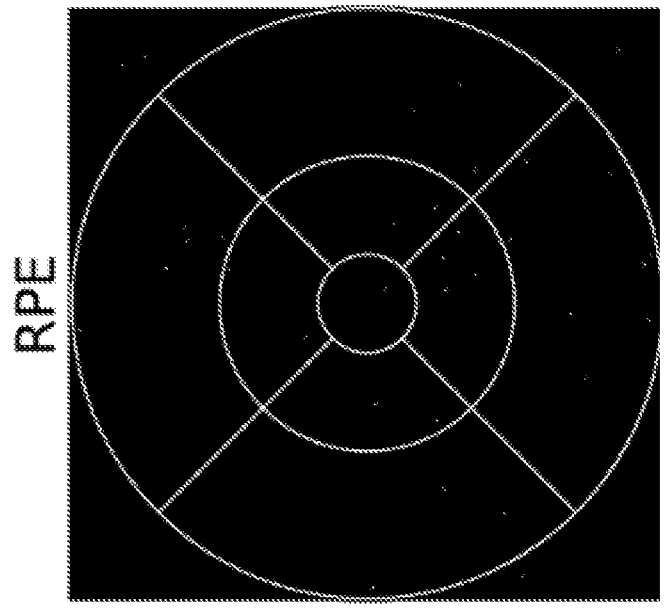
Figure 2G:
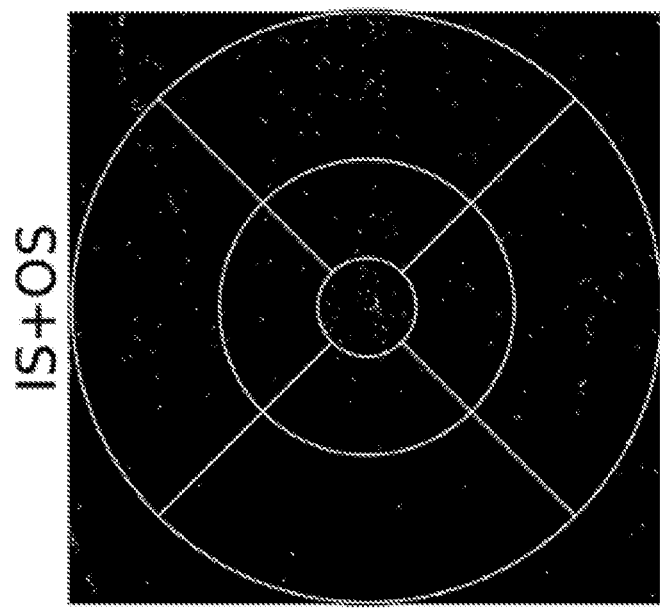
Figure 3A:
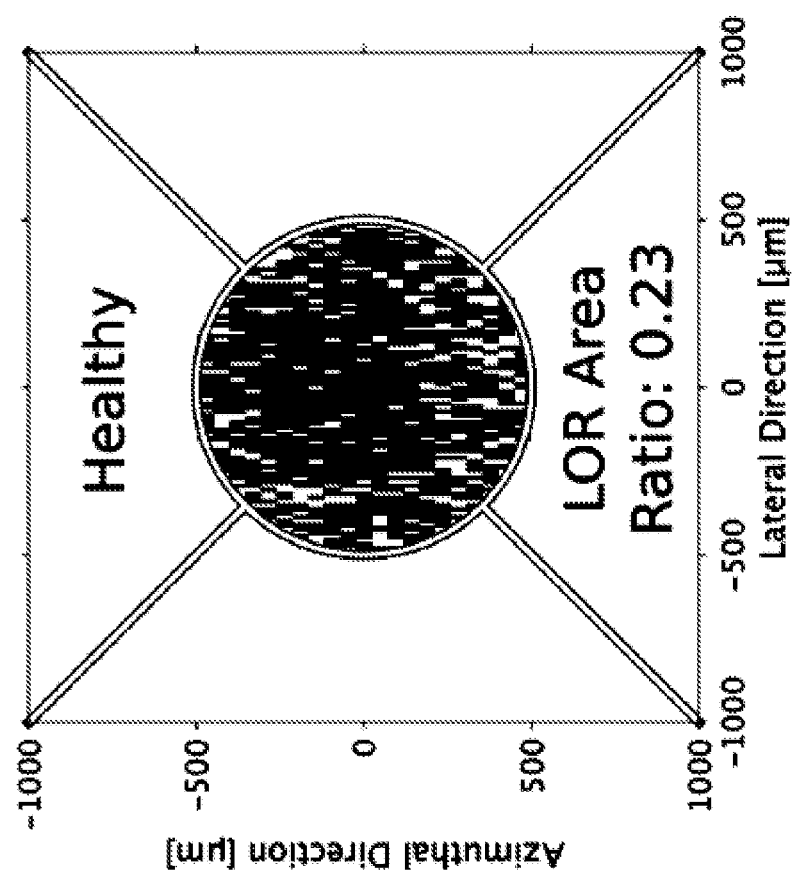
FIGS. 3A-3D—SD-OCT LOR maps for the INL at the Central Subfield—500 μm radius area centered at the fovea—of a healthy subject (FIG. 3A), a NPDR patient (FIG. 3B), a SME patient (FIG. 3C) and a CME patient (FIG. 3D). Sites of SD-OCT low optical reflectivity are identified in white indicating locations of increased extracellular space. SD-OCT LOR area ratios values are 0.23 (FIG. 3A), 0.30 (FIG. 3B), 0.37 (FIG. 3C) and 0.55 (FIG. 3D).
Figure 3B:
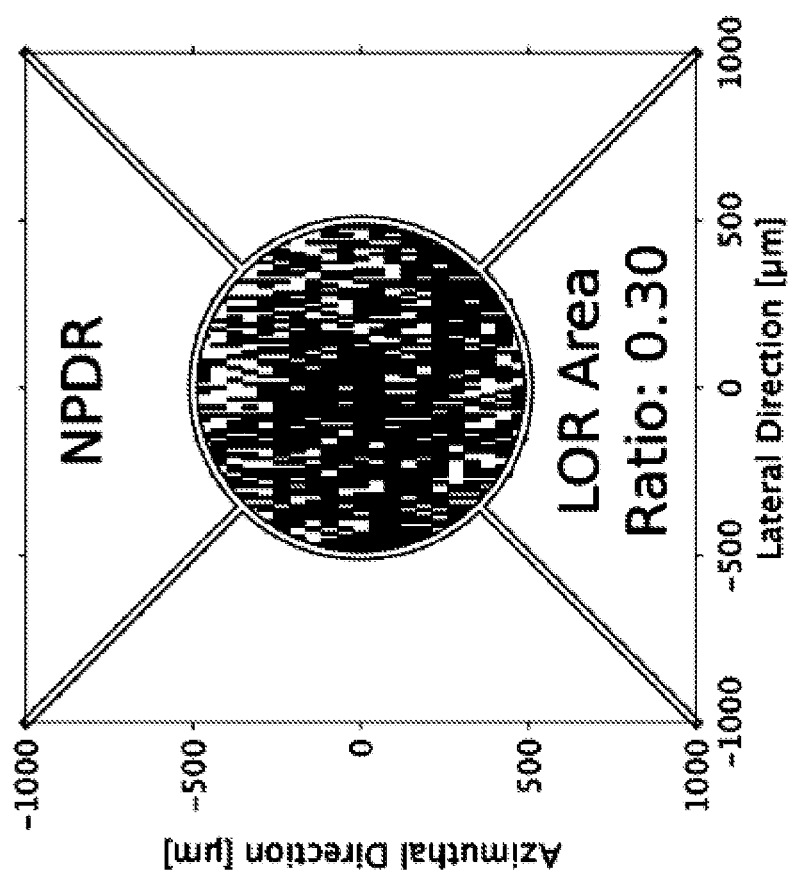
Figure 3C:
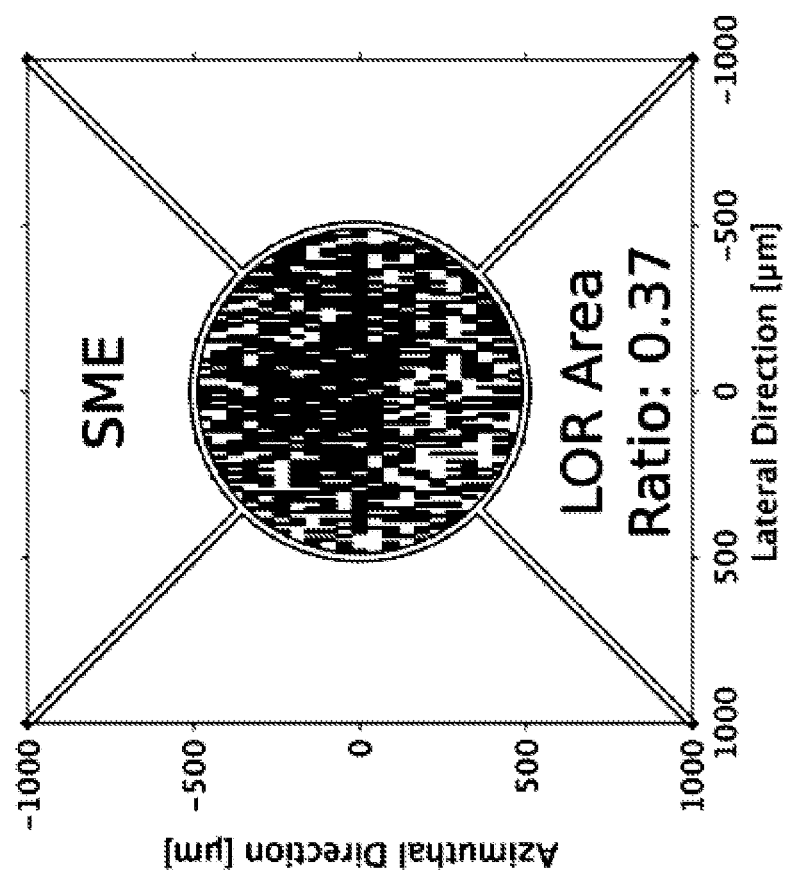
Figure 3D:
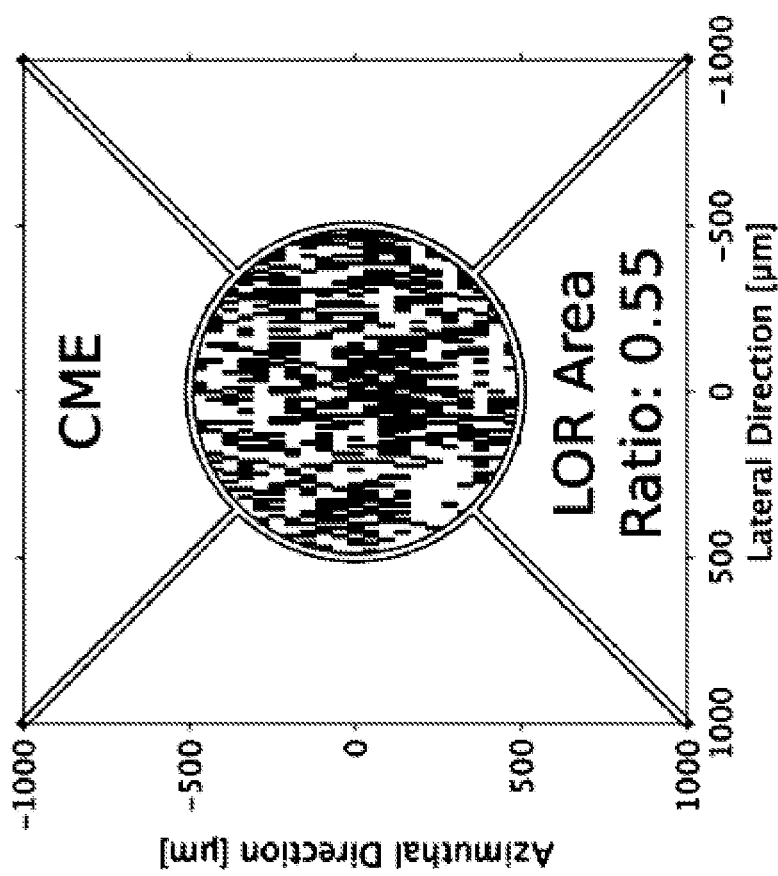
Figure 4B:
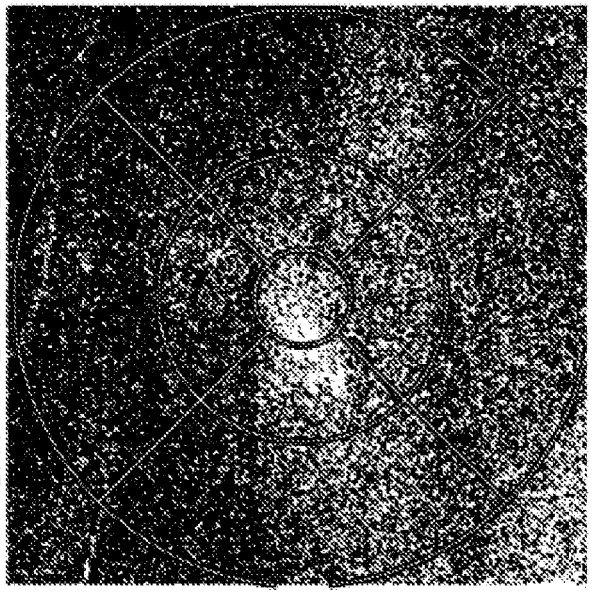
FIGS. 4A-4H—Eye with NPDR and evidence of localized leakage on FA, corresponding well with the increase in extracellular space detected in the OCT-Leakage map of the OPL.
Figure 4A:
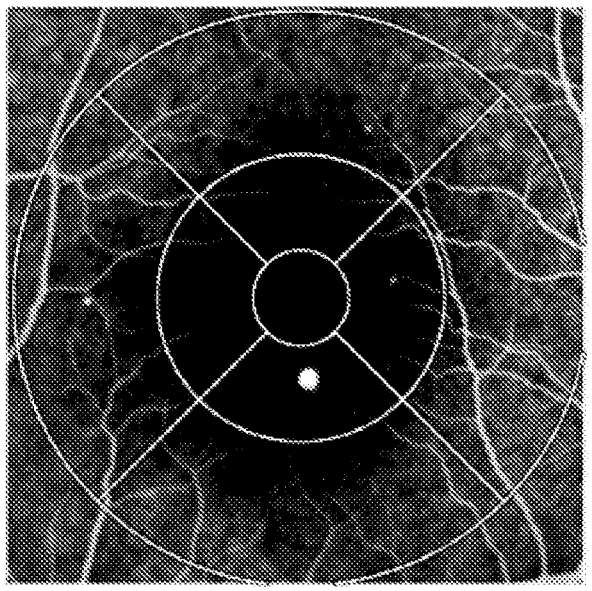
Figure 4D:
Figure 4C:
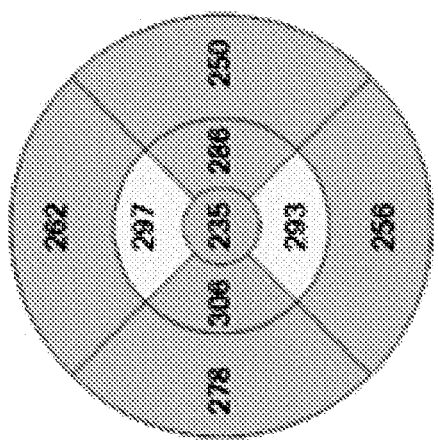
Figure 4F:
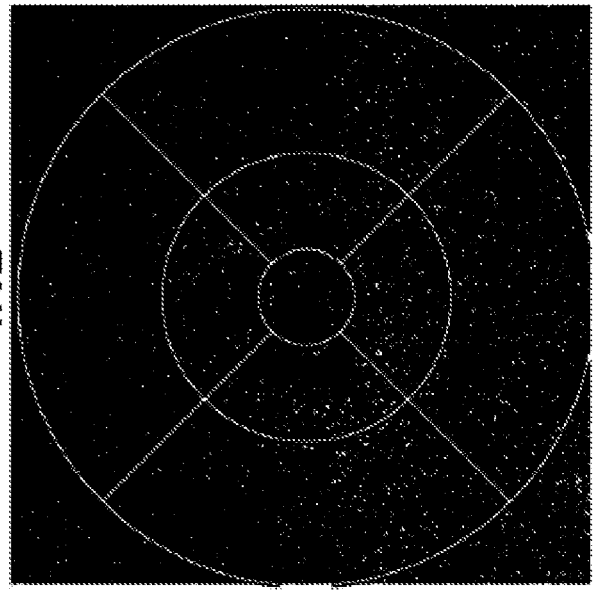
Figure 4E:
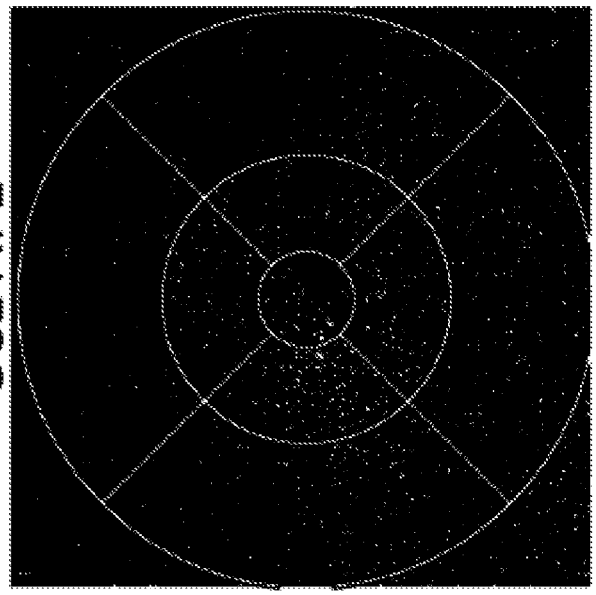
Figure 4H:
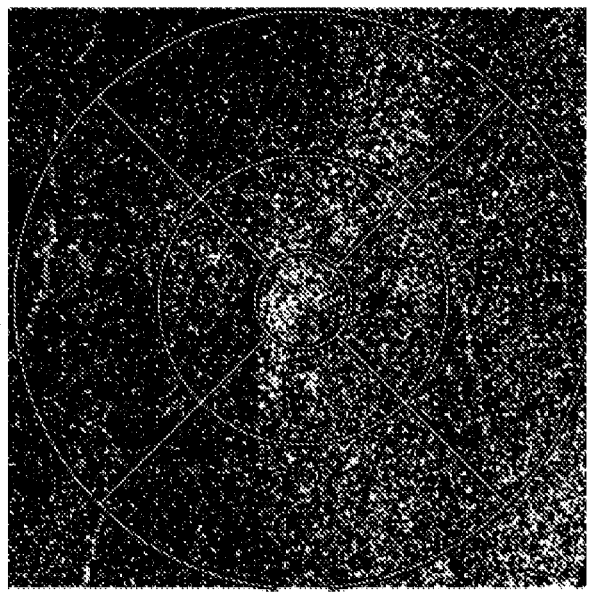
Figure 4G:
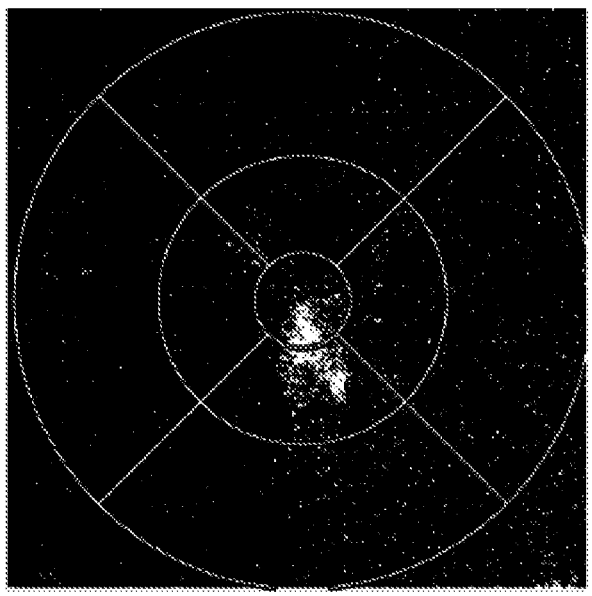
Figure 4J:
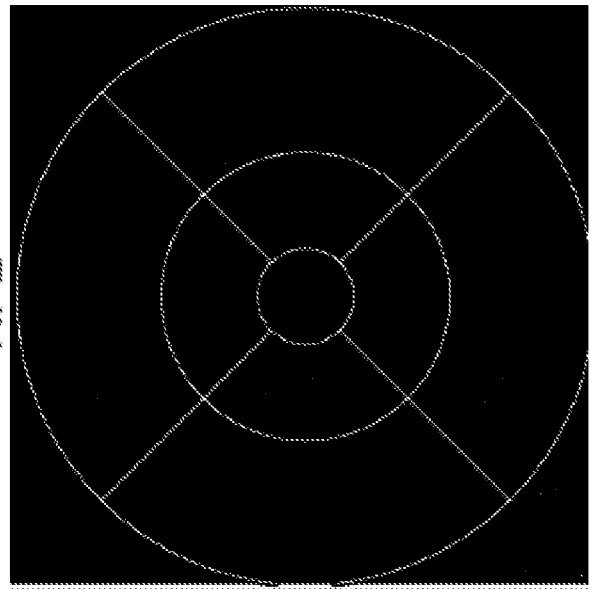
Figure 4I:
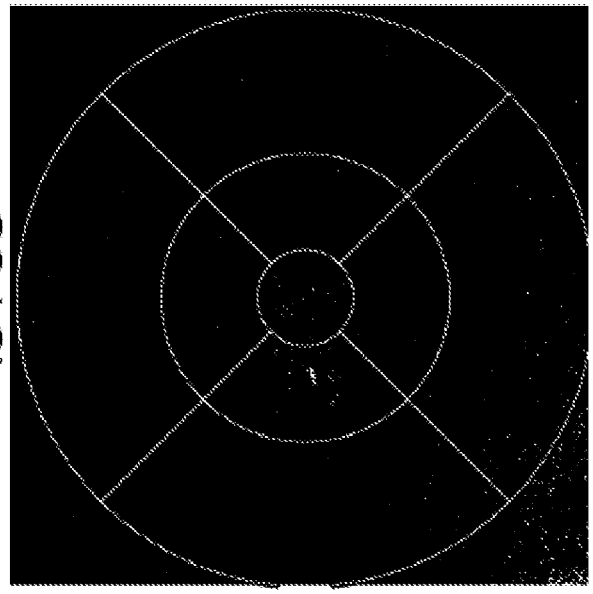

The following regards the determination of low optical reflectivity ratio of a given zone of the retina. Extracellular fluid distribution in the retina is represented on OCT by the distribution of sites of lowest optical reflectivity. Increases or decreases in extracellular fluid distribution of a given area of the retina can, therefore, be measured by the ratio of sites of Low Optical Reflectivity (LOR) identified in the area under evaluation. Analysis of A-Scans from the healthy control retinas allowed us to establish a reflectivity threshold (FIGS. 1A-1C). When A-Scan optical reflectivity value is below the chosen threshold, the location of the A-Scan is identified as a location of LOR and considered for quantification of the LOR area ratio.

The following regards comparing LOR ratios to RT and to fluorescein leakage locations. Calculation of mean and standard deviation values of LOR area ratios and RT, as well as the percentage increase of these from normal values, were performed on a layer by layer basis for each area of the ETDRS grid that consist of a central subfield diameter 1 mm, an inner set of 4 perifoveal subfields with inner diameter of 1 mm and outer diameter of 3 mm, and an outer set of 4 subfields with inner diameter of 3 mm and outer diameter of 6 mm. For RT normal values the aforementioned retinal layer thickness normative database was used while normal values for the LOR area ratios were calculated resorting to the healthy control group.

The following regards results, specifically the location of RT changes on the different retinal layers. An example of the distribution of LOR for the different retinal layers from an ANGIOPLEX™ OCT (angiography tool)—Angiography examination on a healthy eye is represented in FIGS. 2A-2H.

When comparing thickness values of the segmented retinal layers from diabetic SME and CME eyes to the retinal thickness values of the same segmented retinal layer on healthy control eyes it is apparent that there is a selective thickening of the different layers contributing to the overall thickening of the retina (Table 1). This is more clearly so for the INL in the central subfield as this layer thickness shows a higher percentage increase relative to the normative database of 45.20% for NPDR patients with SME and 98.26% for NPDR patients with CME (Table 1). A clear increase in thickness also occurs in retinal layers located next to the INL, the OPL and GCL, particularly as the RT progresses to the stage of CME.

TABLE 1

RT values for the Central Subfield obtained from the different segmented retinal layers showing on the left side the mean and standard deviation values. On the right side, average difference to the layer thickness normative database and its percentage value.

| | Central Subfield | | | | | | | |
|---|---|---|---|---|---|---|---|---|
| | Healthy (N = 25) | | NPDR (N = 10) | | SME (N = 30) | | CME (N = 8) | |
| | Mean [μm] | SD [μm] | Mean [μm] | SD [μm] | Mean [μm] | SD [μm] | Mean [μm] | SD [μm] |
| RNFL | 6.56 | 2.80 | 4.64 | 2.37 | 6.34 | 2.96 | 9.00 | 4.06 |
| GCL + IPL | 45.17 | 8.11 | 40.15 | 6.41 | 48.42 | 6.88 | 58.60 | 7.20 |
| INL | 17.62 | 3.75 | 19.90 | 6.64 | 24.74 | 4.37 | 33.78 | 5.14 |
| OPL | 23.21 | 3.20 | 23.69 | 5.93 | 29.01 | 5.47 | 33.07 | 5.74 |
| ONL | 107.52 | 8.65 | 110.25 | 9.35 | 121.78 | 8.84 | 124.58 | 11.28 |
| OS + IS | 44.19 | 2.34 | 43.89 | 2.53 | 43.89 | 5.10 | 44.52 | 1.57 |
| RPE | 25.15 | 2.81 | 25.33 | 2.39 | 25.08 | 2.62 | 24.56 | 2.28 |

| | Central Subfield | | | | | | | |
|---|---|---|---|---|---|---|---|---|
| | Healthy | | NPDR | | SME | | CME | |
| | Diff [μm] | % | Diff [μm] | % | Diff [μm] | % | Diff [μm] | % |
| RNFL | 0.64 | 10.89 | −1.28 | −21.56 | 0.42 | 7.14 | 3.08 | 52.10 |
| GCL + IPL | 1.19 | 2.70 | −3.83 | −8.71 | 4.44 | 10.11 | 14.62 | 33.25 |
| INL | 0.58 | 3.41 | 2.86 | 16.78 | 7.70 | 45.20 | 16.74 | 98.26 |
| OPL | 1.96 | 9.22 | 2.44 | 11.48 | 7.76 | 36.52 | 11.82 | 55.64 |
| ONL | −2.89 | −2.62 | −0.16 | −0.14 | 11.37 | 10.30 | 14.17 | 12.83 |
| OS + IS | −1.21 | −2.66 | −1.51 | −3.32 | −1.51 | −3.33 | −0.88 | −1.94 |
| RPE | −0.71 | −2.75 | −0.53 | −2.05 | −0.78 | −3.01 | −1.30 | −5.02 |

The following pertains to an analysis of SD-OCT LOR area ratios in the Central Subfield. An analysis was performed separately for each of the segmented layers generating for each one an SD-OCT optical reflectivity map for the diabetic eyes, with NPDR only, with NPDR and SME and NPDR with CME, and compared with healthy control eyes (FIGS. 3A-3D and Table 2).

The SD-OCT optical reflectivity images identify well the changes in extracellular space and their distribution in the macular region. Lower optical reflectivity represented by more clear spaces is well demonstrated in the INL when comparing central subfields from patients with different degrees of edema (FIGS. 3A-3D). In the eyes examined there was a good correlation between increases in retinal thickness and LOR area ratios in the INL and OPL (Table 2).

eye with diabetic CME and localized fluorescein leakage, the FA leakage site is identified well in the INL but the increase in extracellular space is predominant in the ONL. Finally, in FIGS. 6A-6J, an eye with branch retinal vein occlusion and evidence of localized fluorescein leakage on FA, shows that the extracellular space increases identified by the LOR ratios correlate well with the site of fluorescein leakage on FA. In this eye, there is major alteration of the INL but other retinal layers are also involved to different degrees suggesting different levels of tissue damage.

The following regards results, specifically the OCT-Leakage identification of sites of alteration of the BRB in other retinal diseases besides DR. The methodology here presented shows the sites of leakage identified by FA in other retinal diseases besides diabetes. The location of extracel-

TABLE 2

Comparison between of SD-OCT LOR area ratio and percentage of change of layer thickness from normative values for the Healthy, NPDR, SME and CME eyes in the central subfield.

| | | Healthy N = 25 | | NPDR N = 10 | | SME N = 30 | | CME N = 8 | |
| --- | --- | --- | --- | --- | --- | --- | --- | --- | --- |
| | | LOR Area Ratio | Thickness Change Percentage | LOR Area Ratio | Thickness Change Percentage | LOR Area Ratio | Thickness Change Percentage | LOR Area Ratio | Thickness Change Percentage |
| RNFL | Avg. | 0.12 | 10.89 | 0.14 | −21.56 | 0.14 | 7.14 | 0.18 | 52.10 |
| | S. Dev. | 0.05 | 47.29 | 0.04 | 40.10 | 0.06 | 49.96 | 0.04 | 68.65 |
| GCL + | Avg. | 0.31 | 2.70 | 0.43 | −8.71 | 0.43 | 10.11 | 0.55 | 33.25 |
| IPL | S. Dev. | 0.06 | 18.44 | 0.07 | 14.56 | 0.11 | 15.64 | 0.07 | 16.38 |
| INL | Avg. | 0.22 | 3.41 | 0.34 | 16.78 | 0.39 | 45.20 | 0.51 | 98.26 |
| | S. Dev. | 0.06 | 22.00 | 0.10 | 38.95 | 0.11 | 25.67 | 0.05 | 30.14 |
| OPL | Avg. | 0.27 | 9.22 | 0.38 | 11.48 | 0.40 | 36.52 | 0.46 | 55.64 |
| | S. Dev. | 0.05 | 15.05 | 0.09 | 27.90 | 0.10 | 25.74 | 0.09 | 27.02 |
| ONL | Avg. | 0.93 | −2.62 | 0.96 | −0.14 | 0.97 | 10.30 | 0.97 | 12.83 |
| | S. Dev. | 0.04 | 7.83 | 0.03 | 8.47 | 0.03 | 8.01 | 0.02 | 10.22 |
| OS + IS | Avg. | 0.14 | −2.66 | 0.19 | −3.32 | 0.18 | −3.33 | 0.23 | −1.94 |
| | S. Dev. | 0.04 | 5.16 | 0.05 | 5.57 | 0.08 | 11.24 | 0.12 | 3.45 |
| RPE | Avg. | 0.02 | −2.75 | 0.02 | −2.05 | 0.02 | −3.01 | 0.03 | −5.02 |
| | S. Dev. | 0.01 | 10.87 | 0.01 | 9.25 | 0.01 | 10.13 | 0.01 | 8.83 |

The following regards results, specifically the correspondence between sites of fluorescein leakage and sites of low optical reflectivity. The co-registration procedure described earlier allowed us to map fluorescein leakage locations identified in the FA image onto the ANGIOPLEX™ OCT (angiography tool) Angiography data, so locations of OCT low optical reflectivity and leakage could be compared. There is good correspondence between the location of increased LOR area ratios and sites of fluorescein leakage in FA. The changes in extracellular space, represented by the LOR area ratio corresponded well with the main sites of leakage on the FA exams. Similar correlations were found for all eyes with NPDR and other retinal diseases examined by FA and the OCT-Leakage method. Representative cases are illustrated in FIGS. 4A-4J, 5A-5J and 6A-6J.

It is to be noted that the LOR ratios identify well the main sites of leakage and also the areas of late leakage shown in FA. Furthermore, the areas of late leakage on FA are identified by sites of increased extracellular space in specific retinal layers, demonstrating different involvement in different eyes of the different retinal layers. It became apparent from the examinations performed that as the severity of leakage increased there was more involvement of the neighboring retinal layers of the INL.

In FIGS. 4A-4J, an eye with NPDR with localized leakage on FA, the LOR ratios reflecting increase in the extracellular space are mainly located in the OPL indicating more damage and tissue disruption in this retinal layer. In FIGS. 5A-5J an lular space increases identified well the leakage sites and, furthermore, the involvement of the different retinal layers in eyes with central serous chorioretinopathy, macular edema after cataract surgery and branch retinal vein occlusion (FIGS. 6A-6J).

The following regards the complementarity of OCT-Leakage with OCT-Microangiography to replace FA. The co-registration procedures described allowed also co-identification of the areas of increased LOR ratios with sites of fluorescein leakage in FA and their correlation with microvascular alterations detected by OCT-Microangiography. This co-identification is well demonstrated in FIGS. 7A-7J.

The figures show the increased visibility of the retinal vascular lesions demonstrated by OCT-Microangiography and the location of increases in extracellular space involving different layers of the retina.

Combination of OCT-Leakage and OCT-Microangiography methodologies allow (1) visualization of the traditional angiography distribution and its alteration which can be well-recognized by clinicians using FA, (2) identification of cross-sectional structural OCT images, locating the alterations in the retina, (3) identification and localization of sites of low LOR ratio, i.e., areas of increased extracellular space corresponding to alterations of the BRB, and (4) identification of sites of neovascularization and capillary dropout in the retinal vasculature.

In this disclosure we describe an automated OCT based method to identify and quantify increases in the retinal extracellular space which are surrogate indicators of breakdown of the BRB, using a non-invasive OCT-based methodology.

Breakdown of the BRB is a frequent alteration occurring in the retina due to diabetes and other retinal vascular diseases and has major clinical implications. It is of major relevance that the presently available therapies for macular edema act mainly by correcting the alteration of the BRB. Monitoring the alterations of the BRB is, therefore, of major clinical relevance.

FA is used routinely in clinical practice, to show and demonstrate alterations of the BRB, but is an invasive method relying on intravenous injection of fluorescein which may be associated to severe adverse events.

Recently, OCT-Microangiography has become available replacing much of the information given by FA, such as visualization of areas of capillary dropout in a non-invasive manner. However, OCT-Microangiography cannot visualize dye leakage, i.e., alteration of the BRB [3].

In this disclosure, we demonstrate that it is possible to reliably locate and quantify increases in the retinal extracellular space in diabetic patients and that the changes in the retinal extracellular space correlate well with the occurrence and degree of retinal edema. Furthermore, localized increases in the retinal extracellular space identify in the same location the areas of fluorescein leakage seen on FA. The method of OCT-Leakage based on the determination of LOR-ratios allows the identification of the main sites of leakage (i.e., alteration of BRB) and the areas of leakage visible on late FA images. Furthermore, OCT-Leakage is able to identify the location of the increases of retinal extracellular space in the different layers of the retina thus being able to identify the retinal cells more affected and the potential impact of the retinal tissue damage. This information is expected to offer new insights into the progression and recovery of macular edema with particular value regarding prognosis for visual acuity recovery.

In summary, the method and device here described is able to detect and locate non-invasively, the sites of leakage, i.e., alteration of the BRB in retinal diseases, being, therefore, expected to replace FA. It offers, furthermore, an added value by identifying the changes occurring in the different layers of the retina.

OCT-Leakage location and quantification is able to complement OCT-Microangiography thus allowing full information on the retinal circulation namely capillary closure, vascular morphology and alteration of BRB by using non-invasive OCT based methodologies. OCT techniques may, therefore, replace the widely used method of FA which is invasive and associated with risks.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

It is to be appreciated that certain embodiments of the invention as described herein may be incorporated as code (e.g., a software algorithm or program) residing in firmware and/or on computer useable medium having control logic for enabling execution on a computer system having a computer processor, such as any of the servers described herein. Such a computer system typically includes memory storage configured to provide output from execution of the code which configures a processor in accordance with the execution. The code can be arranged as firmware or software, and can be organized as a set of modules, including the various modules and algorithms described herein, such as discrete code modules, function calls, procedure calls or objects in an object-oriented programming environment. If implemented using modules, the code can comprise a single module or a plurality of modules that operate in cooperation with one another to configure the machine in which it is executed to perform the associated functions, as described herein.

The disclosure should not be seen in any way restricted to the embodiments described and a person with ordinary skill in the art will foresee many possibilities to modifications thereof.

The above described embodiments are combinable.

The following claims further set out particular embodiments of the disclosure.

The invention claimed is:

1. An automated method for detecting and quantifying sites of abnormal extracellular fluid in a retina, from optical coherence tomography ("OCT") data of an eye, wherein said data comprises OCT A-scans over an area of the eye and each OCT A-scan data comprises a series of optical reflectivity values along a depth direction of the OCT A-scan, said method comprising:
   segmenting the OCT A-scan data into retinal layers;
   detecting and quantifying sites for each segmented retinal layer on each OCT A-Scan having an optical reflectivity value lower than a predetermined threshold, wherein the detecting and quantifying for each OCT A-scan is carried out independently of thresholding for neighboring OCT A-scans; and
   generating, of each retinal layer, a two dimensional en-face image comprising the detected sites.

2. The method of claim 1, wherein the threshold is predetermined according to optical reflectivity values of a healthy population.

3. The method of claim 1, wherein the predetermined threshold is 20 when measured using an a spectral domain OCT imaging instrument that uses of a light source centered at 840 nm with a 50 nm bandwidth and provides a 5 μm axial resolution in tissue to image a 6×6×2 mm$^3$ or a 3×3×2 mm$^3$ volume of the retina by 350×350×1024 or 245×245×1024 voxels, respectively, as manufactured by Zeiss and is 10 when measured using a spectral domain OCT imaging instrument having an acquisition speed of 27,000 A-Scans per second to image a 6×6×2 mm$^3$ volume of the retina by 512×128×1024 voxels with 5 μm axial and 20 μm lateral resolutions as manufactured by Zeiss.

4. The method of claim 1, further comprising: previously obtaining the OCT A-scans over the area of the eye.

5. The method of claim 1, wherein segmenting retinal layers from the OCT A-scan data is carried out according to an optical reflectivity of each identified retinal layer.

6. The method of claim 5, wherein the step of segmenting retinal layers from the OCT A-scan data comprises graph-theory segmentation.

7. The method of claim 1, further comprising: preprocessing the OCT A-scan data, said preprocessing comprising one or more of speckle reduction or normalization operations.

8. The method of claim 1, wherein the steps of the method are carried out pixel by pixel of the two dimensional image corresponding to the area of the eye.

9. The method of claim 8, further comprising: displaying said images by a computer display and/or storing said images in a data storage media.

10. The method of claim 9, further comprising: displaying OCT-Microangiography data in the computer display side-by-side or superimposed with en-face images of an optical reflectivity of each of the segmented retinal layers.

11. The method of claim 1, wherein the segmenting step further comprises: segmenting the OCT A-scan into 6 to 11 retinal layers.

12. The method of claim 1, wherein the detected sites for each OCT A-scan having a reflectivity value lower than the predetermined threshold are identified as sites of alterations of the blood-retinal barrier.

13. A non-transitory data storage media device, comprising: program instructions for implementing a device for detecting sites of low optical reflectivity from optical coherence tomography ("OCT"), the program instructions including instructions executable to carry out the method of claim 1.

14. The device of claim 13, further comprising: an electronic data processor configured to execute the program instructions.

15. A system for detecting sites of low optical reflectivity from optical coherence tomography ("OCT") in accordance with the method of claim 1, comprising:
an electronic data processor;
a non-transitory data storage media device comprising program instructions for implementing a device for detecting sites of low optical reflectivity from optical coherence tomography ("OCT"), the program instructions including instructions executable to carry out the method of claim 1;
OCT equipment suitable for detecting sites of low optical reflectivity, wherein the OCT equipment is a spectral domain OCT imaging instrument that uses of a light source centered at 840 nm with a 50 nm bandwidth and provides a 5 μm axial resolution in tissue to image a 6×6×2 $mm^3$ or a 3×3×2 $mm^3$ volume of the retina by 350×350×1024 or 245×245×1024 voxels, respectively, as manufactured by Zeiss or a spectral domain OCT imaging instrument having an acquisition speed of 27,000 A-Scans per second to image a 6×6×2 $mm^3$ volume of the retina by 512×128×1024 voxels with 5 μm axial and 20 μm lateral resolutions as manufactured by Zeiss; and
a display for displaying the detected sites of low optical reflectivity.

16. The method of claim 1, wherein the segmenting step further comprises segmenting the OCT A-scan into 7 retinal layers.

* * * * *